United States Patent [19]

Silberstein

[11] Patent Number: 5,331,969

[45] Date of Patent: *Jul. 26, 1994

[54] EQUIPMENT FOR TESTING OR MEASURING BRAIN ACTIVITY

[75] Inventor: Richard B. Silberstein, Victoria, Australia

[73] Assignee: Swinburne Limited, Victoria, Australia

[*] Notice: The portion of the term of this patent subsequent to Sep. 11, 2007 has been disclaimed.

[21] Appl. No.: 561,976

[22] Filed: Aug. 2, 1990

Related U.S. Application Data

[63] Continuation-in-part of Ser. No. 35,610, Mar. 30, 1987, Pat. No. 4,955,388.

[30] Foreign Application Priority Data

Dec. 22, 1989 [AU] Australia .................... PJ8006/89
Jun. 26, 1990 [AU] Australia .................... PK0824/90

[51] Int. Cl.$^5$ .................................................. A61B 5/04
[52] U.S. Cl. .................................... 128/731; 128/745; 364/413.05
[58] Field of Search .................. 128/731, 732, 745; 364/413.02, 413.05

[56] References Cited

U.S. PATENT DOCUMENTS

| | | | |
|---|---|---|---|
| 3,855,998 | 12/1974 | Hidalgo-Briceno | 128/745 |
| 3,901,215 | 8/1975 | John | 128/745 |
| 3,998,213 | 12/1976 | Price | 128/644 |
| 4,216,781 | 8/1980 | John | 128/731 |
| 4,407,299 | 10/1983 | Culver | 128/731 |
| 4,462,411 | 7/1984 | Rickards | 128/731 |
| 4,493,539 | 1/1985 | Cannon, Jr. | 128/731 |
| 4,537,198 | 8/1985 | Corbett | 128/639 |
| 4,566,464 | 1/1986 | Piccone et al. | 128/731 |
| 4,632,122 | 12/1986 | Johansson et al. | 128/644 |
| 4,649,482 | 3/1987 | Raviv et al. | 128/731 |
| 4,665,499 | 5/1987 | Zacharski et al. | 128/731 |
| 4,676,611 | 6/1987 | Nelson et al. | 128/731 |
| 4,794,533 | 12/1988 | Cohen | 128/731 |
| 4,832,480 | 5/1989 | Kornacker et al. | 128/731 |
| 4,861,154 | 9/1989 | Sherwin et al. | 128/731 |
| 4,862,359 | 8/1989 | Trivedi et al. | 364/413.05 |
| 4,878,498 | 11/1989 | Abrams et al. | 128/731 |
| 4,892,106 | 1/1990 | Gleeson, III | 128/745 |
| 4,913,160 | 4/1990 | John | 128/731 |
| 4,932,416 | 6/1990 | Rosenfeld | 128/731 |
| 4,974,602 | 12/1990 | Abraham-Fuchs et al. | 128/731 |
| 4,977,896 | 12/1990 | Robinson et al. | 128/653 R |

FOREIGN PATENT DOCUMENTS 2604889  4/1988  France.
WO87/00745  2/1987  PCT Int'l Appl. ............. 128/731

OTHER PUBLICATIONS

English translation of abstract specification of French Patent 2604889 dated Apr. 15, 1988 (Miszcazak; et al) cited above.

Proceedings of the Eleventh Annual Northeast Bioengineering Conference, Mar. 14, 15, 1985, Worcester Polytechnic Institute, Worcester, Massachusetts, Walter S. Kuklinski and William J. Ohley, pp. 128–134.

Descriptive Linear Modeling of Steady-State Visual Evoked Response by William H. Levison, Andrew M. Junker and Kevin Kenner, Proceedings of the Twenty-First Annual Conference on Manual Control, Jun. 17–19, 1985, Ohio State University, Columbus Ohio pp. 1.1–1.16.

J. Ciociari et al., "The Multichannel Electrode Helmet," Proceedings Conference on Engineering And (List continued on next page.)

Primary Examiner—Stephen C. Pellegrino
Assistant Examiner—Guy V. Tucker
Attorney, Agent, or Firm—Wolf, Greenfield & Sacks

[57] ABSTRACT

Electrical activity of the brain is analysed by the application of a repetitive stimulus so as to evoke a steady state response, changes or differences in the steady state response being used as a measure of said electrical activity. The spatial distribution of the activity can be displayed as a topographical representation of the brain, which representation can be updated so as to provide a substantially real-time display. A neuro-psychiatric workstation incorporating such a display can be used for instance for various research purposes.

45 Claims, 21 Drawing Sheets

OTHER PUBLICATIONS

Physical Sciences In Medicine, Melbourne, p. 52 (1987) (abstract only).

J. Dubinsky et al., "A Simple Dot-Density Topogram For EEG," Electroenceph. Clin. Neurophysiol., vol. 48, pp. 473-477 (1980).

R. Galambos et al., "Dynamic Changes In Steady-State Responses," In E. Basar (Ed) Springer Series In Brain Dynamics, I. Springer-Verlag, Berlin Heidelberg, pp. 103-122 (1988).

J. Johnstone et al., "Regional Brain Activity In Dyslexic And Control Children During Reading Tasks: Visual Probe Event-Related Potentials," Brain And Language, vol. 21, pp. 233-254 (1984).

A. Junker et al., "The Effect Of Task Difficulty On The Steady State Visual Evoked Response," 1986 IEEE, pp. 905-908.

W. R. Klemm et al., "Hemispheric Lateralization And Handedness Correlation Of Human Evoked 'Steady-State' Responses To Patterned Visual Stimuli," Physiological Psychology, vol. 8, pp. 409-416 (1980).

D. Regan, "Steady-State Evoked Potentials," Journal of the Optical Society of America, vol. 67, pp. 1475-1489 (1977).

M. A. Schier et al., "Requirements Of A High Spatial Resolution Brain Electrical Activity Data Acquisition System." Neuroscience Letters, Suppl. 30, p. S151 (1988) (abstract only).

R. B. Silberstein et al., "Topographic Distribution of the Steady State Visually Evoked Potential," Neuroscience Letters, Suppl. 30, p. S123 (1988) (abstract only).

P. S. Sebel et al., "Evoked Responses—A Neurophysiological Indicator of Depth Of Anaesthesia?", British Journal of Anaesthesia, vol. 57, No. 9, pp. 841-842 (Sep. 1985).

G. F. Wilson et al., "Steady State Evoked Responses: Correlations With Human Cognition," Psychophysiology, vol. 23, p. 57 (1986) (abstract only).

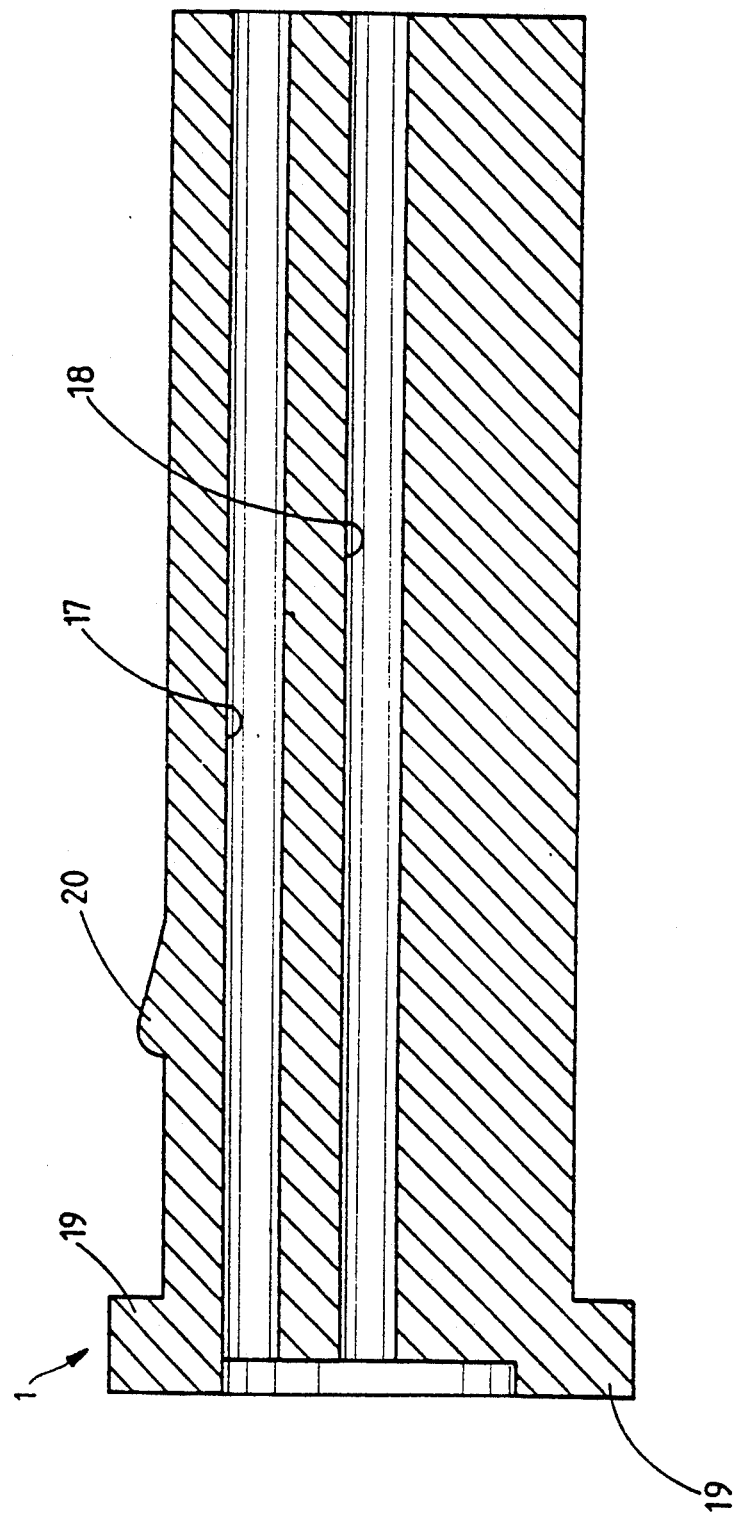

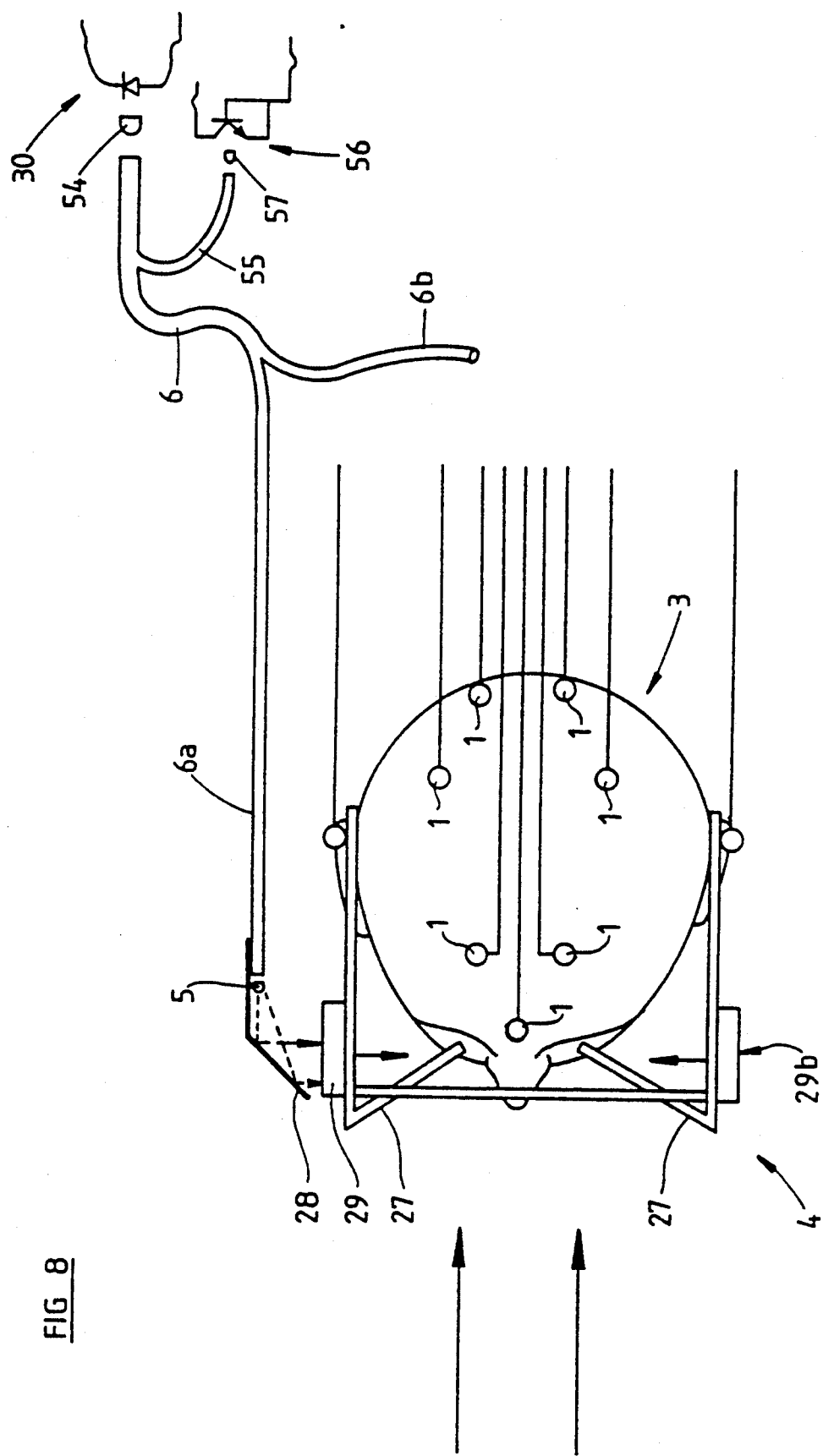

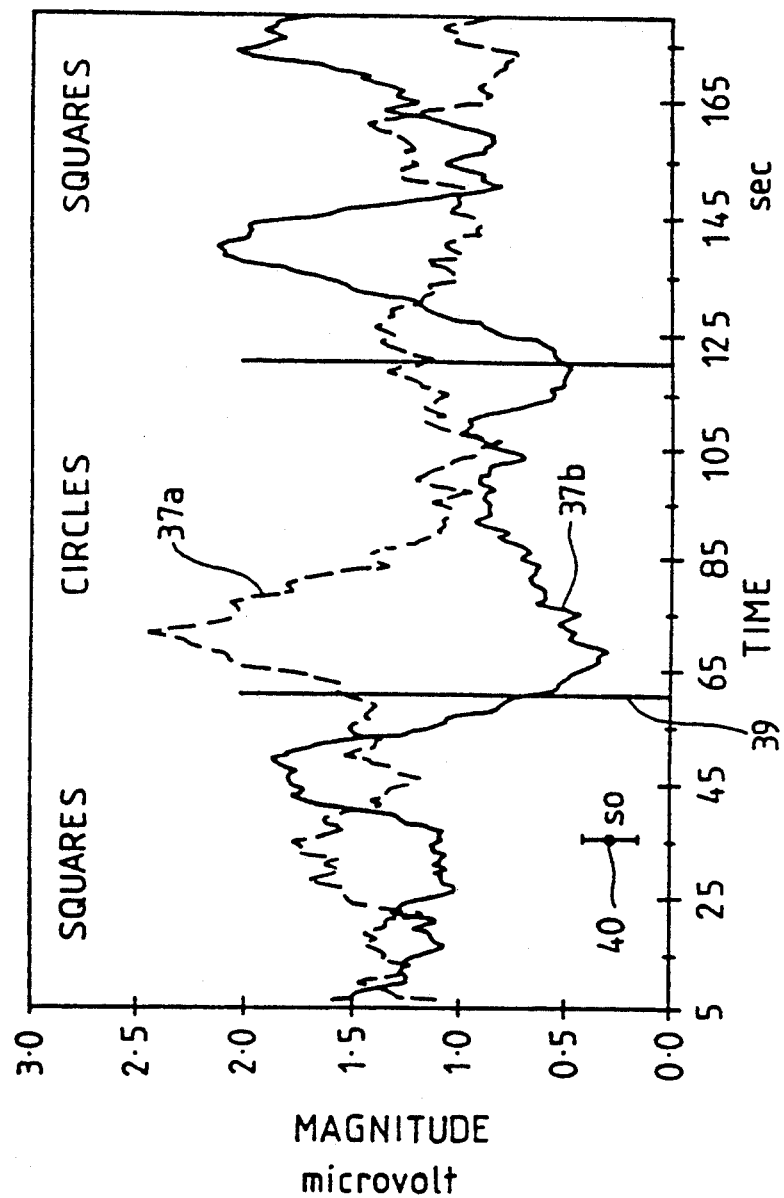

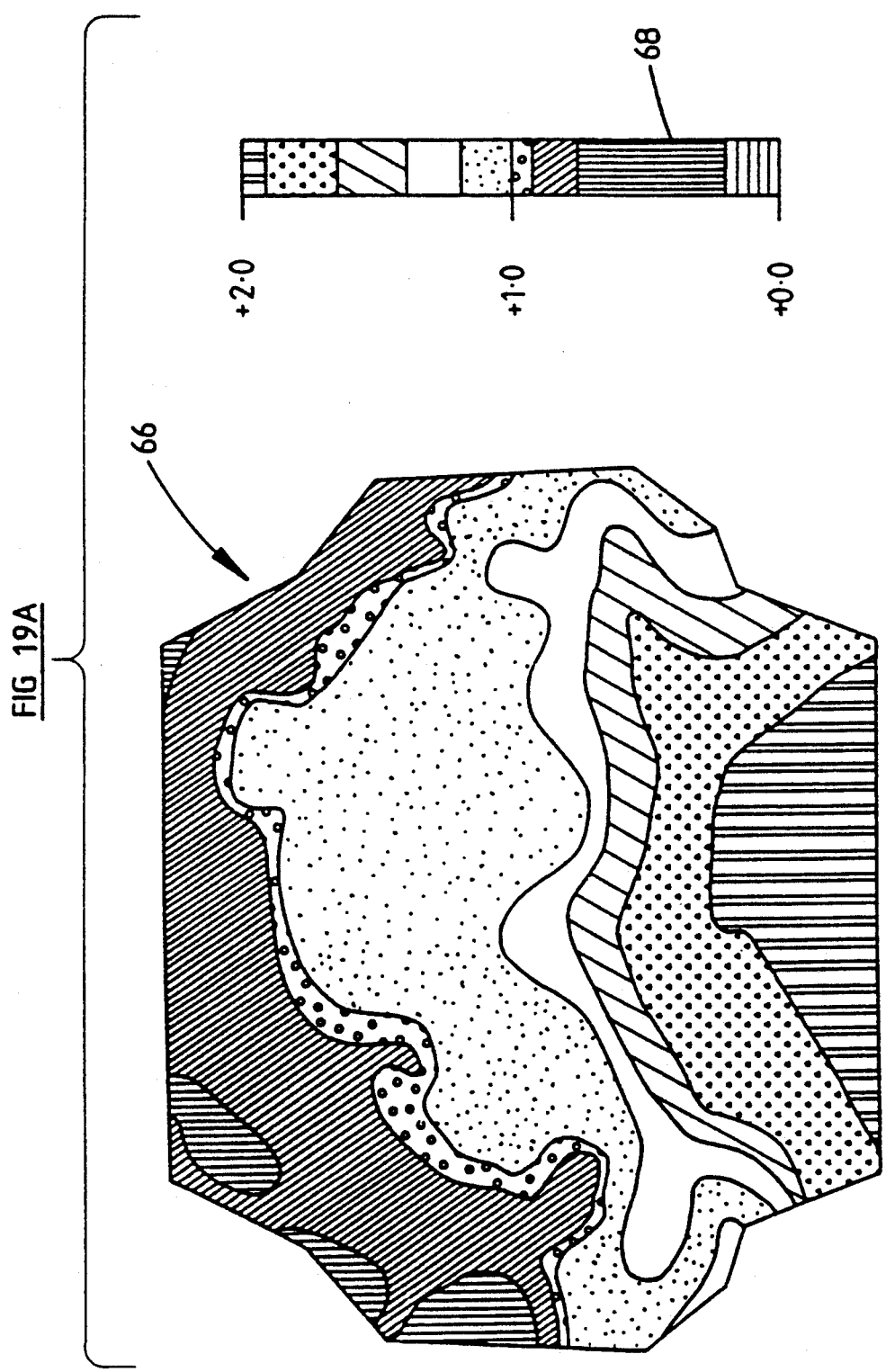

EQUIPMENT FOR TESTING OR MEASURING BRAIN ACTIVITY

This application is a continuation-in-part of co-pending application Ser. No. 07/035,610 entitled "Electroencephalographic Attention Monitor", filed Mar. 30, 1987, now U.S. Pat. No. 4,955,388.

BACKGROUND OF THE INVENTION

1. Field of the Invention

The present invention relates to equipment for testing or measuring brain activity, and may take the form of a neuropsychiatric workstation.

2. Description of the Prior Art

Please note the following discussion makes reference to publications which are detailed subsequently under the heading "Reference Publications".

Numerous studies have been undertaken into the effects of cognition on Event Related Potentials (ERPs) (see review Gevins and Cutillo 1986). The majority of these studies have utilized discrete and discontinuous stimuli such as auditory clicks, tones or the tachistoscopic presentation of visual targets. These stimuli are associated with what have been termed "transient" ERPs (Regan 1977) and constitute the familiar sequence of waveforms widely reported (e.g. McGillen & Aunon 1987). By contrast there have been relatively few reported studies concerning cognitive effects on the evoked potentials associated with rapidly repetitive stimuli. Potentials evoked by such stimuli have been termed "Steady State Evoked Potentials" and consist of sinusoidal components at the stimulus frequency or multiples of the stimulus frequency (Regan 1977, 1989).

The Steady Stare Potential has an attractive feature relevant to the study of cognitive processes, this being the ability to assess the characteristics of the potential in as little as 10 seconds (Regan 1989). This would make it an ideal instrument to investigate time varying phenomena in cognitive processes. In spite of this attractive feature there has been a dearth of studies demonstrating a relationship between the Steady State Evoked Potential and cognitive processes.

Galambos (Galambos & Makeig 1985, 1988) has drawn attention to the fluctuations in the human auditory Steady State Evoked Potential and has considered the relationship between these and cognitive processes. While these fluctuations were originally thought to be associated with "shifts in arousal" (Galambos & Makeig 1985), more recent reports from this group failed to uncover any relationship between cognitive processes and the auditory steady state potential (Galambos & Makeig 1988). In an extensive study, Linden et al (1987) were unable to demonstrate any effects of selective attention on the auditory steady state evoked potential. This was despite the fact that the same subjects yielded strong selective attention effects in the late components of the transient ERP.

While no feature of the auditory steady state potential has yet been demonstrated to be correlated with cognitive processes, recent studies concerning the Steady State Visually Evoked Potential (SSVEP) have yielded a relationship with cognitive processes. Wilson & O'Donnell (1986) reported that the rate of memory scanning, as determined by the Sternberg memory scanning task, (Sternberg 1969), is correlated with the apparent latency of the SSVEP. The apparent latency was calculated from the SSVEP phase versus stimulus frequency plot, a method described by Regan (1989). Specifically, subjects with shorter apparent SSVEP latencies scanned through the list of memory items faster. This occurred when the stimulus frequency was in the range 15-35 Hz. While this correlation indicated a relationship between the speed of cognitive processes and the SSVEP latency, it did not yield a relationship between a change in cognitive function, such as attention, and a corresponding change in the SSVEP. In a subsequent study by this group, the specific issue of the relationship between cognitive processes and the SSVEP was addressed when considering the effects of mental workload on the SSVEP (Wilson & O'Donnell 1988). They reported that the SSVEP appeared relatively insensitive to mental workload. This suggests a weak effect of cognitive processes on the SSVEP in the frequency ranges investigated.

Referring now to a technique known as the Probe-ERP technique, a premise is that regional increases in cortical activity associated with the cognitive processes will in turn give rise to smaller potentials evoked by an irrelevant (or probe) stimulus (Papanicolaou & Johnstone 1984). This premise is supported by findings which indicate a reduction in the transient Probe-ERP being associated with an increase in regional cerebral bloodflow (Papanicolaou 1986).

A number of Probe-ERP studies have demonstrated ERP correlates of cognitive processes. Specific examples include a finding that the attenuation of an auditory probe ERP was larger in the left hemisphere during a covert articulation task (papanicolaou et al 1983). This Probe-ERP indication of left hemisphere specialization for certain language tasks was reinforced by a more recent report indicating that auditory probe magnetic fields were more attenuated in the left hemisphere during a task involving the identification of a phonological target (Papanicolaou et al 1988). In a reading task, left temporal attenuation of the visual probe ERP was correlated with task difficulty (Johnstone et al 1984). By contrast, a visuo-spatial task requiring subjects to mentally rotate geometrical figures yielded visual probe attenuation which was greatest in the right parietal region. In another study involving a visuo-spatial task, a simultaneous measurement of regional cerebral bloodflow and the visual probe ERP demonstrated concurrent right parietal probe ERP attenuation and increased regional cerebral bloodflow (Papanicolaou et al 1987).

Reference Publications

Bucsbaum, M., Rigal, F., Coppola. R., Cappalletti, J., King, C. and Johnson, J. (1982). A new system for gray-level surface distribution maps of electrical activity. Electrenceph. clin Neurophysiol 53:237-242.

Ciorciari J., Silberstein R. B., Simpson D. G. and Schier M. A. (1987). The multichannel electrode helmet. Proceedings Conference on Engineering and Physical Sciences in Medicine, Melbourne 1987. pp52.

Courchesne, E., Elmasian, R. and Yeung-Courchesne (1987) Electrophysiological correlates of cognitive processing: P3b and Nc, basic, clinical and developmental research. In (Eds) A. M. Halliday, S. R. Butler and R. Paul; A Textbook of Clinical Neurophysiology. John Wiley & Sons pp 645-676.

Deutsch, G., Papanicolaou, C., Bourbon, W. T. and Eisenberg, H. M. (1987). Cerebral blood flow evidence of right frontal activation in attention demanding tasks. Intern. J. Neuroscience 36:23-28.

Dubinsky, J and Barlow, J. S. (1980). A simple dot-density topogram for EEG. Electroenceph. clin. Neurophysiol 48: 473–477.

Fuster, J. M. (1980). The prefrontal cortex. Academic Press: New York.

Fuster, J. M., Baurer, R. H., and Jervey, J. P. (1982). Cellular discharge in the dorso lateral prefrontal cortex of the monkey in cognitive tasks. Experimental Neurology. 77: 679–694.

Gevins, A. S. (1986) Overview of computer analysis. In A. S. Gevins and A. Remond (Eds). Methods of analysis of brain electrical and magnetic signals (Handbook of electroencephalography and clinical neurophysiology; new ser. V1) Amsterdam: Elsevier. pp 31–84.

Gevins, A. S. and Cutillo, B. A. (1986). Signals of cognition. In F. H. Lopes da Silva, W. Storm van Leeuwen and A. Remond (Eds). Clinical applications of computer analysis of EEG and other neurophysiological signals (Handbook of electroencephalography and clinical neurophysiology; new ser. V2). Amsterdam: Elsevier. 335–384.

Galambos, R. and Makeig, S. (1985). Studies on the auditory high-rates responses: Methods and major findings. Abstract in Proceedings of International conference on Dynamics of sensory and cognitive processing in the brain, 20.

Galambos, R. and Makeig, S. (1988). Dynamic changes in Steady-state Responses. In E. Basar (Ed) Springer Series in Brain Dynamics 1. Springer-Verlag, Berlin Heidelberg, pp 103–122.

Halliday, A. M., Barrett, G., Halliday, E. and Michael, W. F. (1977). The topography of the pattern-evoked potential. In J. E. Desmedt (ed) Visual evoked potentials in man: New developments pp 121–133.

Janisse, M. P. (1977). Pupillometry: the psychology of the pupillary response. Hemisphere Publication Corporation: Washington Johnstone, J., Galin, D., Fain, G., Yingling, C., Herron, J and Marcus, M. (1984) Regional brain activity in dyslexic and control children during a reading task: Visual probe event-related potentials. Brain and Language., 21, 233–254.

Klemm, W. R., Gibbons, W. D., Allen, R. G. and Richey, E. O. (1980). Hemispheric lateralization and handedness correlation of human evoked "steady state" responses to patterned visual stimuli. Physiological Psychology, 8:409–416.

Linden, R. D., Picton, T. W., Hamel, G and Campbell K, B (1987). Human auditory evoked potentials during selective attention. Electroenceph. clin. Neurophysiol., 66:145–159.

McGillen C. D., Aunon J. I. (1987). Analysis of Event-related potentials. pp131-169 in Gevins A. S., Remond A. (ads.) Methods of Analysis of Brain Electrical and Magnetic Signals. Handbook of Electroencephalography and Clinical Neurophysiology. Vol 1.Elsevier, Amsterdam, 1987.

Mazziotta, J. C. and Phelps, M. E. (1984). Human sensory stimulation and deprivation: Positron emission tomographic results and strategies. Ann Neurol Suppl 15:50–60

Mountcastle, V. B. (1978). Brain mechanisms for directed attention. R. Soc. Med 71:14–27

Mesulam, M-M. (1981) A cortical network for directed attention and unilateral neglect. Ann Neurol., 10, 309–325.

Milner, B. and Petrides, M. (1984). Behavioral effects of frontal-lobe lesions in man. Trends in Neurosciences 403–407.

McCallum, W. C. (1988) Potentials related to expectancy, preparation and motor activity. In T. W. Picton (Ed) Human Event-Related Potentials. (Handbook of Electroencephalography and Clinical Neurophysiology; new ser. V3) Elsevier: Amsterdam pp 427–534.

Oldfield, R. C. (1971) The assessment and analysis of handedness: The Edinburgh Inventory. Neuropsychologia, 9, 73–113.

Papanicolaou, A. C., Deutsch, G., Bourbon, W. T., Will, K. W., Loring, D. W. and Eisenberg, H. M. (1987) Convergent evoked potential and cerebral blood flow evidence of task-specific hemispheric differences. Electroenceph. clin. Neurophysiol., 66, 515–520.

Papanicolaou., A. C., Eisenberg, H. M. and Levy, R. S. (1983) Evoked potential correlates of left hemisphere dominance in covert articulation. Intern J Neuroscience., 20, 289–284.

Papanicolaou A. C., Johnstone J. (1984). Probe Evoked Potentials: theory method and applications. International Journal of Neuroscience. 24:107–131.

Papanicolaou, A. C., Wilson, G. F., Busch, C., DeRego, P., Orr, C., Davis, I and Eisenberg, H. M. (1988) Hemispheric asymmetries in phonological processing assessed with probe evoked magnetic fields. Intern J Neurosciences, 39:275–281.

Papanicolaou, A. C., Schmidt, A. L., Moore, B. D. and Eisenberg, H. M. (1983). Cerebral activation patterns in an arithmetic and visuospatial processing task. Intern J Neurosciences., 20:283–288.

Poggio, G. F. (1980). Central neural mechanisms in vision. In V. B. Mountcastle (Ed) Medical Physiology. Mosby, St Louis. pp544–585.

Regan, D. (1977). Steady-state evoked potentials. Journal of the Optical Society of America, 11, 1475–1489.

Regan, D. (1989) Human brain electrophysiology: evoked potentials and evoked magnetic fields in science and medicine. Elsevier, New York 1989.

Roland, P. E. (1984). Metabolic measurements of the working frontal cortex in man. Trends in Neurosciences 430–435.

Schier, M. A., Ciorciari, J., Silberstein, R. B. and Simpson D. G. (1988) Requirements of a high spatial resolution brain electrical activity data acquisition system. Neuroscience Letters., Suppl 30, S151.

Silberstein R. B., Ciorciari J., Musci F., Schier M. A., Simpson D. G. (1988) Topographic distribution of the steady state visually evoked potential. Neuroscience Letters Supplement 30: S 123.

Simpson, R., Vaughan, Jr., H. G., and Ritter, W. (1976). The scalp topography of potentials associated with missing visual or auditory stimuli. Electroenceph. Clin. Neurophysiol. 40, pp 33–42.

Spitzer, A. R., Cohen, L. G., Fabrikant, J and Mallet, M. (1989) A method for determining optimal interelectrode spacing for cerebral topographic mapping. Electroenceph. Clin. Neurophysiol., 72, 355–361.

Stapleton, J. M., O'Reilly, T., and Halgren, E. (1987). Endogenous potentials evoked in simple cognitive tasks: scalp topography. Intern. J. Neurosciences. 36: pp 75–87.

Sternberg, S. (1969). The discovery of processing stages: Extension of Donders method. Acta Psychologia, 30, 276–315.

Sutton, S., and Ruchkin, D. S. (1984). The late positive complex: advances and new problems. In (Eds) R. Karrer, J. Cohen, and P. Tueting, Brain and Information Event-related Potentials. Ann. N.Y. Acad..Sci., 425, 1-23.

Walsh, K. W. (1978). Neuropsychology: A clinical approach. Churchill Livingstone, Edinbrugh.

Walter, W. G. (1967) Slow potential changes in the human brain associated with expectancy, decision and intention. In W. Cobb and C. Morocutti (Eds). The Evoked Potentials. Electroenceph. clin. Neurophysiol., (Suppl.) 26, pp. 123-130.

Weintraub, S. and Mesulam, M-M (1987) Right cerebral dominance in spatial neglect. Arch Neurol., 44, 621-625.

Wilson, G. F. and O'Donnell, R. D. (1986) Steady state evoked responses: Correlation with human cognition. Psychophysiology, 23, 57-61.

Wilson, G. F. and O'Donnell, R. D. (1988). Measurement of operator workload with the neuropsychological workload test battery, in: (Eds) Hancock, P. A. and Meshkati, N. Human mental workload, Elsevier Science Publishers B. V. (North-Holland) pp 63-100.

SUMMARY OF THE INVENTION

The reported insensitivity of the SSVEP to cognitive processes could have been due to a number of factors. Firstly, Wilson & O'Donnell (1986, 1988) appear to have only examined the correlation between apparent SSVEP latency and mental workload. The effects of mental workload may have been reflected in changes in SSVEP amplitude rather than latency. In addition, only the central occipital and central parietal sites were investigated (Oz, Pz), thus changes in the SSVEP occurring at other sites or lateralized effects would not have been observed.

According to the present invention, work has now been done, as a result of which a new approach has been developed. This new approach, "Steady State Probe Topography", possesses a number of distinct advantages in the study of cognitive processes. Firstly, it appears possible to measure electrophysiological effects associated with cognitive processes in as few as one trial. Secondly, the continuous nature of the response permits an opportunity of examining the dynamics of cortical activity on a time scale from one to two seconds to hours. A "Steady State Probe Paradigm" according to an embodiment of the present invention can provide a sensitive indicator of regional brain activity associated with cognitive processes.

An object of the present invention is therefore to provide equipment for testing or measuring brain activity which is relatively versatile in operation and which can be used to investigate brain activity which occurs over a relatively short period.

A workstation according to an embodiment of the invention may be generally directed to assessing brain activity in response to cognitive tasks such as card sorting or attention tasks, and an example may generally be described as equipment for testing or measuring brain activity, such as a neuropsychiatric workstation, comprising means for measuring spatially distributed changes in a response of the brain to a distinguishable control stimulus, and means for displaying a representation of said changes in relation to said brain, as an indication of the extent and spatial distribution of said electrical activity with respect to the brain.

Preferably the stimulus is such as to generate a steady state response in the brain and may for instance comprise a sinusoidal stimulus.

Conveniently the stimulus comprises a visual stimulus, such a light input to the eye which varies in intensity. However, other stimuli may be substituted.

Preferably, means is provided for updating said representation at a rate comparable to a real-time display.

Overall, a neuropsychiatric workstation according to an embodiment of the present invention can provide an integrated biomedical testing system that utilises the brain's responses to a series of cognitive tests (called tasks or probes) to provide a detailed analysis of the patterns of complex functioning that the brain is capable of undertaking.

Embodiments may also detect the onset of epileptic activity and respond by terminating a dangerous stimulus. The equipment concerned may be generally well isolated against noise or voltage surges by the use of optical or inductive couplings.

Further advantages and features of the invention will be apparent from the following description and the appended drawings, all of which illustrate an embodiment of the invention which is not intended to limit the scope of the invention in any way.

BRIEF DESCRIPTION OF THE DRAWINGS

FIGS. 6, 7a and 7b show in cross section and electrode, and a electrode locator, for use with the helmet of FIG. 4;

FIG. 8 shows schematically in plan view an arrangement for applying a visual stimulus to a subject by means of goggles, and picking up responses by means of electrodes applied to the head;

FIGS. 13a and 13b show magnitude time series results measured for a single subject at two different electrode sites;

FIGS. 19a and 19b show the topographic distribution of the cross subject averaged normalised magnitude at the appearance of circles in trials (viewings) 2 and 3.

DESCRIPTION OF THE PREFERRED EMBODIMENT

To assess the possible sensitivity of the SSVEP to cognitive processes, a specific approach was adopted with the following three features:

The probe-ERP technique was employed wherein the ERP stimulus was presented in a manner as to be distinct from and irrelevant to the cognitive task undertaken by the subjects.

Drain electrical activity was recorded from 64 scalp sites within the area defined by the International 10-20 system.

A Fourier analyser with a 10 second integration period was used to determine SSVEP magnitude.

HARDWARE OVERVIEW

Figure 1:
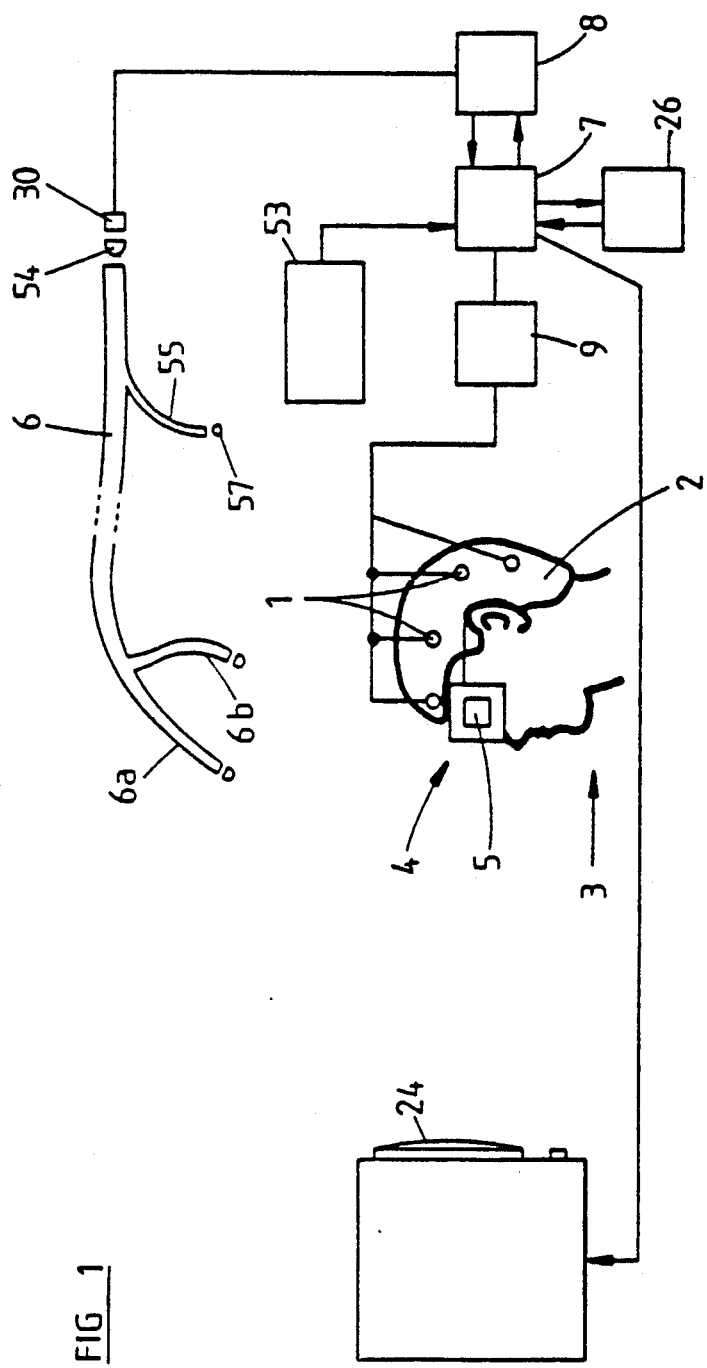
FIG. 1 shows a schematic diagram of equipment according to an embodiment of the present invention.
Figure 2:
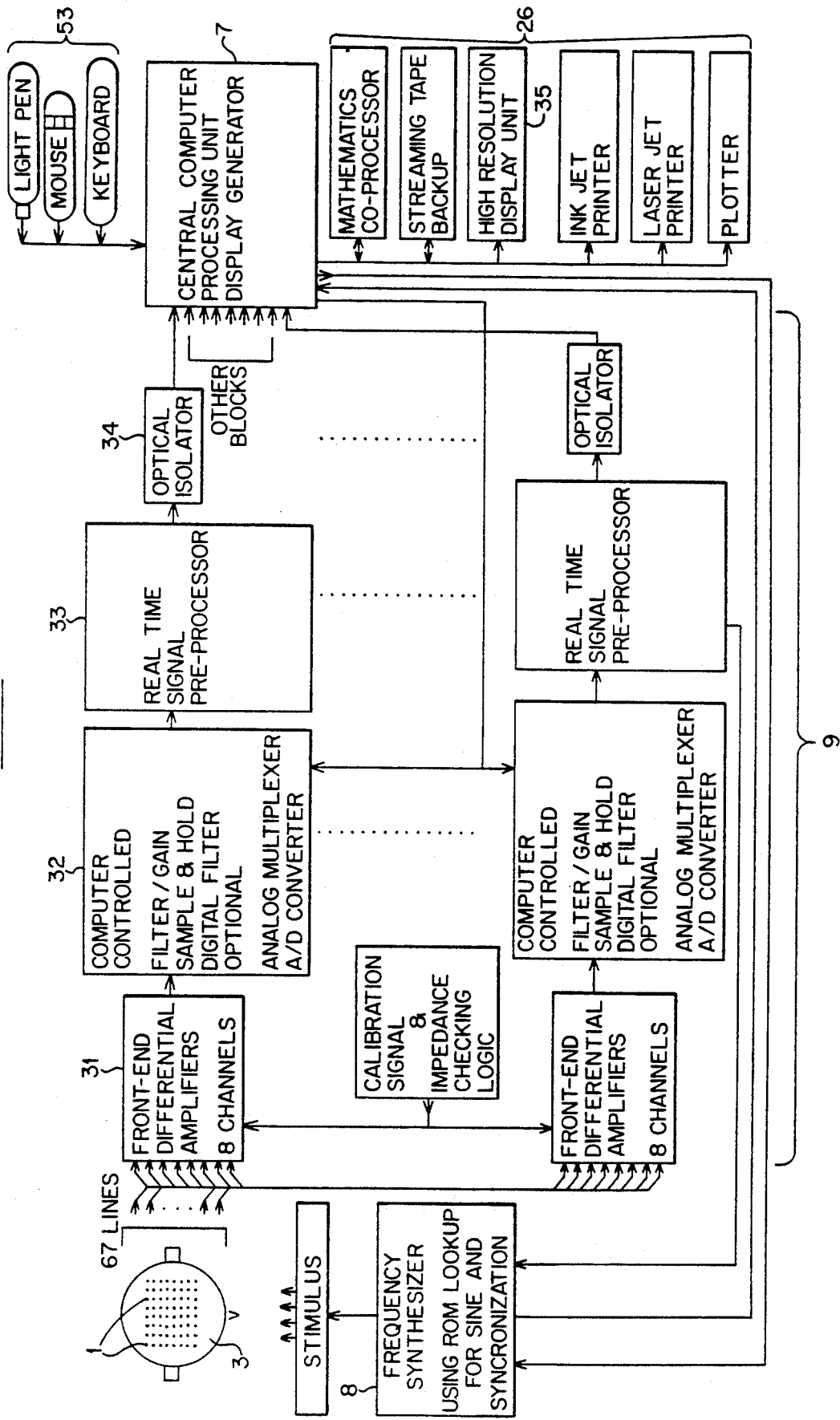
FIG. 2 shows in more detail, and by means of a block diagram, the equipment of FIG. 1.

Referring to FIGS. 1 and 2, the hardware of a specific embodiment of the invention may be generally arranged as follows:

There are 64 electrodes 1 arranged in a helmet 2, the helmet being electrically screened. Stimuli are provided to a subject 3 wearing the helmet 2, by means of a video screen 24 and goggles 4, the goggles having lateral screens 5, which screens are lit from behind by optical fibers (not shown in FIG. 1).

The subject 3 can view the video screen 24 and simultaneously be treated to a visual flicker by means of the lateral screens 5 and the optical fibers. Electrical responses of the brain to these visual stimuli are picked up by the electrodes 1 and analyzed by means of a preprocessing block 9 and central processing unit 7.

The central computer processing unit 7 provides overall control and signal processing. It not only processes the subject's responses but can also control and synchronize both types of stimulus, i.e. displays on the video screen 24 and the flicker stimulus to the goggles 4. Further, the unit 7 provides protection to epileptic subjects by detecting an unusually strong response.

In the receive path between the electrodes 1 and the central processing unit 7, a pre-processing block 9 provides amplification, filtering and digital control with respect to a response signal. The block 9 can also carry out preliminary signal processing.

The central processing unit 7 of the system is used to decide test stimuli (tasks) for the subject 3, record information, put up display maps of electrical activity at the stimulus frequency on a visual display unit 35, and can animate these maps to produce a practically real-time display of 13 Hz images interpolated to give 25 frames per second.

ELECTRODE ARRANGEMENT

Referring to FIGS. 3 to 8, each electrode 1 is mounted in a bore 10 in the helmet 2 by means of a locator 11. (FIG. 8 shows only a small number of the total 64 electrodes, the actual array of electrodes 1 being shown in FIG. 3.) Referring particularly to FIGS. 7a and 7b, each locator 11 comprises a shallow circular sleeve having a circumferential outer lip 12 thereon.

Figure 5A:
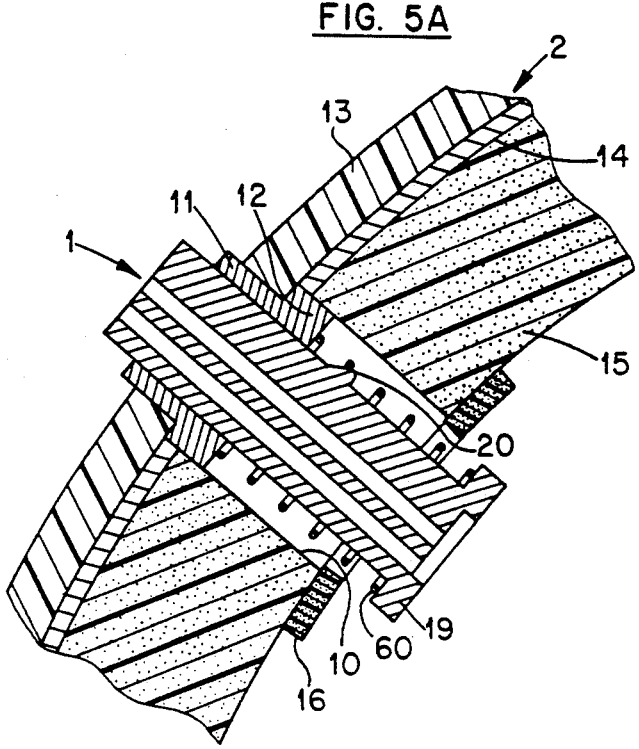

Each locator 11 seats in a bore 10 of the helmet 2, the lip 12 seating against the inside surface of a fiberglass outer shell 13 of the helmet 2, at the margin of the bore 10 (see FIG. 5a). The short sleeve of the locator 11 then projects slightly from the outermost surface of the fiberglass shell 13.

The helmet 2 itself comprises several layers, these being the outer shell 13 referred to and a wire mesh shielding layer 14, within which there is a relatively thick polystyrene foam layer 15 with foam padding 16 on its innermost surface for the comfort of the user. The bore 10 is thus primarily provided by the polystyrene foam layer 15 which is significantly thicker than any other of these layers.

Referring to FIG. 5a, each electrode 1 comprises a barrel having a double bore 17, 18 therethrough, the electrodes 1 having an outwardly directed, circumferential lip 19 at one end, and a small external projection 20 on the barrel, arranged close to the lip 19 but spaced therefrom along the barrel. The external diameter of the barrel of the electrode 1 is the same as the internal diameter of the locator 11. The electrode 1 can thus be mounted in the helmet 2 by inserting the long end of the barrel through a locator 11, from inside the helmet 2. A spring 60 is mounted between the lip 19 of the electrode and the locator 11, acting in a direction to push the electrode 1 inwards with respect to the helmet 2, and therefore against the scalp of a subject 3 wearing the helmet 2. The mounting of an electrode 1 in a locator 11 is shown in FIG. 5A.

Figure 5B:
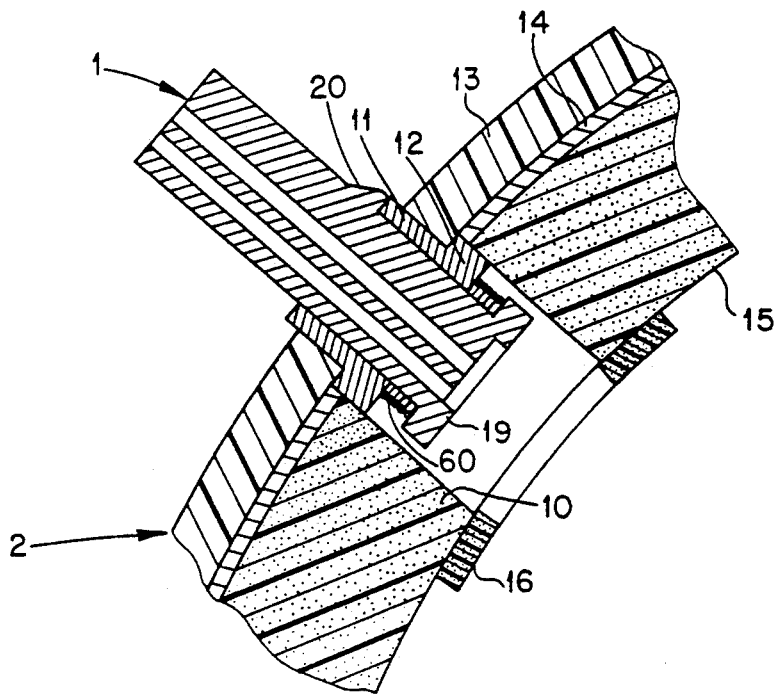
Figure 7A:
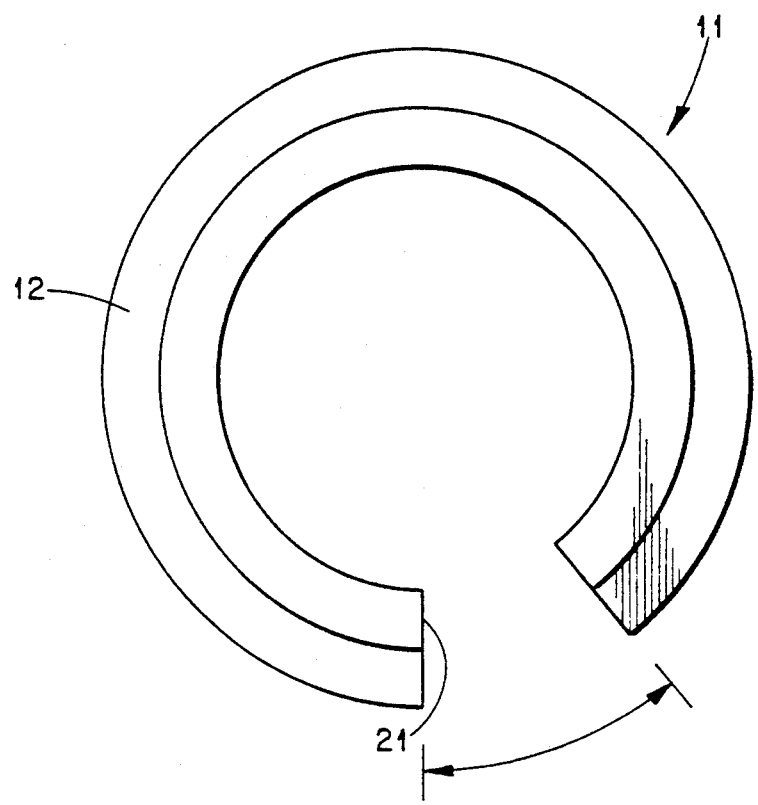
Figure 7B:
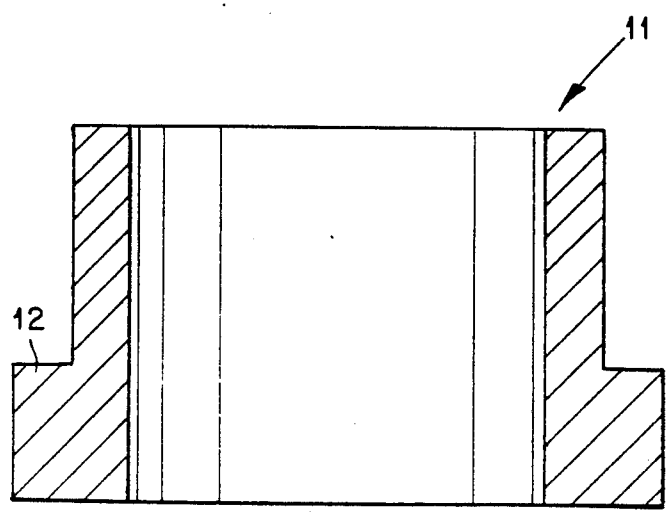

Referring to FIG. 5B, the external projection 20 of the electrode 1 can be used to secure the electrode 1 in a retracted position with respect to a subject's scalp by means of a form of bayonet coupling with the locator 11. This is provided by a limited aperture 21 in the wall of the locator 11, the plan view of the locator 11 as shown in FIG. 7A therefore being substantially "C"-shaped, rather than "O"-shaped. The electrode 1 is retracted, against the action of the spring 60, by bringing the projection 20 through the aperture 21 and rotating the electrode to bring the external projection 20 into a retaining position outside the locator 11, away from the aperture 21. This is convenient of course when only selected electrodes 1 are to be used. It is also convenient for general handling of a helmet 2 when not use, and when being put on or taken off the head of a subject 3.

Figure 4:
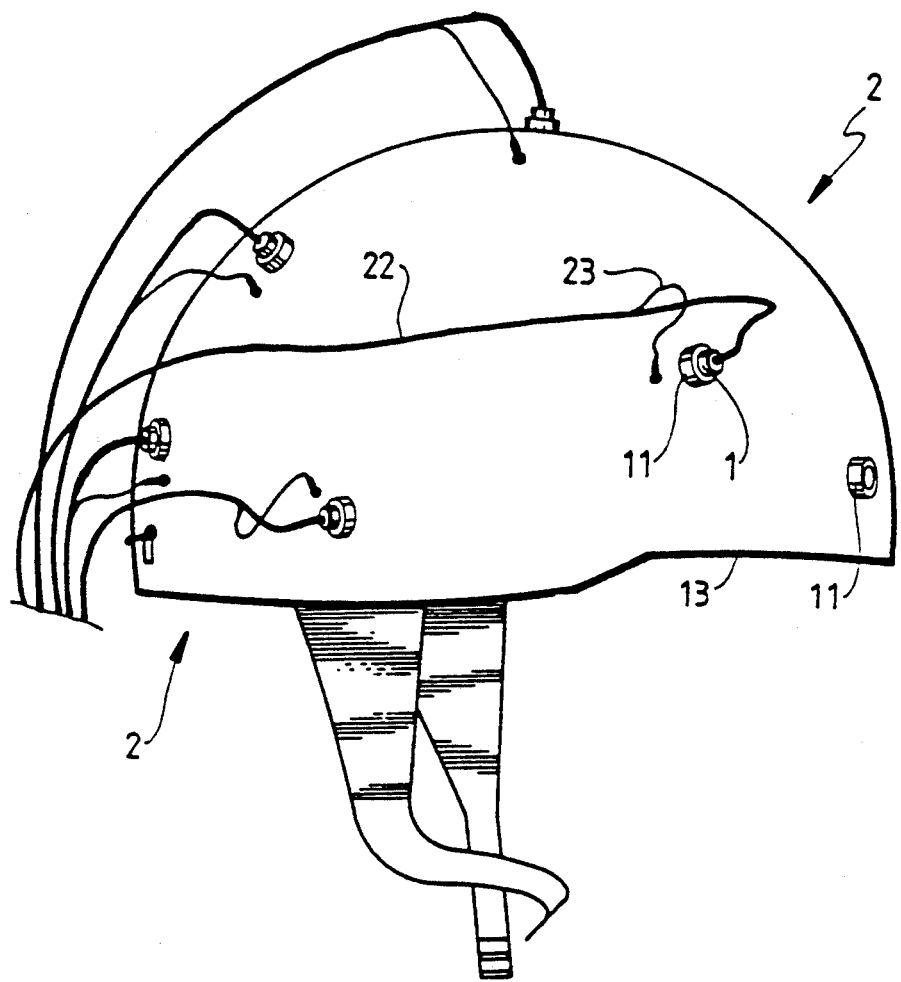
FIGS. 4, 5a and 5b show aspects of a helmet for applying electrodes to sites selected from the sites of FIG. 3.

Referring to FIG. 4, electrical connections 22 are made to each electrode 1, together with an associated earth wire 23 which is secured to the fiberglass shell 13 of the helmet 2 adjacent a respective electrode 1.

The double bore 17, 18 of each electrode 1 allows the provision of an electrically conducting wire (via bore 17), for making an electrical contraction 22, as well as conductive gel (via bore 18) at the surface of a subject's head, once the electrode is in position in a bore 10 of the helmet 2.

Electrode impedances varied from a minimum of 5 kOhm to 35 kOhm when measured at 40 Hz.

PROVISION OF VISUAL STIMULI TO SUBJECT

Figure 9:
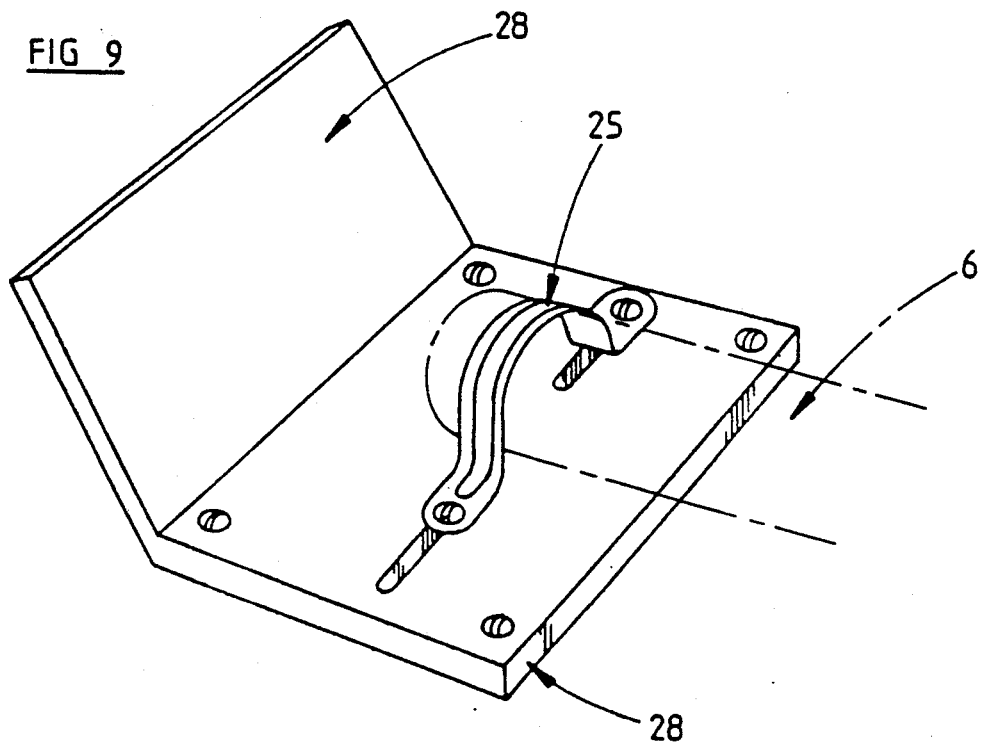
FIG. 9 shows an arrangement using optical fibers to apply the visual stimulus to the goggles of FIG. 8.

Referring to FIGS. 1, 8 and 9, as mentioned above, visual stimuli are supplied to the subject 3 by means of a video screen 24, via specially adapted goggles 4. Further visual stimuli, such as a flicker, can then be superimposed on the same field of view of the subject 3 by means of the goggles 4.

An optical fibre arrangement 6, 6a, 6b delivers the flicker stimulus to the goggles 4, the arrangement being shown schematically only in FIG. 1, without connection between the goggles 4 and the fibers 6a, 6b. The actual connection can be seen in FIG. 8.

Referring to FIG. 8, in order to provide the superimposed visual stimuli, the goggles 4 are provided with semi-reflective screens 27, through which the subject 3 can still view the video screen 24. Optical fibers 6, 6a, 6b then deliver a superimposed flicker stimulus to each semi-reflective screen 27 by means of a reflective directing plate 28 and a diffuser 29. (The arrangement is only shown with respect to the optical fibers 6a on one side of the goggles 4 in FIG. 8, for reasons of clarity, but, in practice, the arrangement is generally symmetrical with a second set of fibers 6b delivering light to a second diffuser 29b on the other side of the goggles 4.)

The optical fibers are secured as a main fibre optic bundle 6 which divides into two bundles 6a, 6b, one held on each side piece of the goggles 4 so as to illuminate the adjacent directing plate 28 and diffuser 29, 29b. Some adjustment of the position of each of the two bundles 6a, 6b is provided by adjustable ties 25 holding the ends of each optical fiber bundle. The end of each fiber bundle 6a, 6b is provided with a lens 5 (one shown only) which spreads the light emitted from the associated bundle 6a, 6b so that it impinges on an enlarged area of the adjacent directing plate 28.

The optical fibre arrangement in general is constructed to have light weight for convenience, and small dimensions. The total length is about 2 meters.

The arrangement is that a view of the video screen 24 providing one of the stimuli is available to a subject 3 through the semi-reflective screens 27, while a different but simultaneous stimulus can be presented via the optical fibers 6.

The superimposed stimulus delivered by the optical fibers 6 can be conveniently generated under the control of the central processing unit 7 as a sinusoidal electrical signal of predetermined frequency, fed to a light emitting diode 30, as indicated on FIG. 1. The end of the main optical fibre bundle 6 remote from the goggles 4 picks up the light output of the "led" 30 via a focusing lens 54, which light output is thus delivered to the semi-reflective screens 27.

Feedback control is provided by means of a small branch 55 of the main optical fibre bundle 6. This is further described below.

The overall arrangement, using fibers 6 to deliver light generated by an "led" 30, has the advantage that potential electrical interference between the "led" 30 and the electrodes 1 of the helmet 2 is avoided by physically separating them by the optical fibers 6.

The field of view covered by the superimposed stimulus can be varied for instance by relative movement between the end of each fiber bundle 6a, 6b and the associated lens 5, or by reselecting the type of lens 5 used. Preferably the whole or substantially the whole of the field of view of a subject 3 through the goggles 4 should be covered by the superimposed stimulus, in most circumstances, although this can of course be departed from.

Instead of a single "led" 30, an array of "leds" can be used to deliver light to the fibres 6. In this case, the spatial extent of the flicker stimulus can be controlled by varying the drive supplied to the "led" array 30 of FIG. 1.

STIMULUS GENERATION

Referring to FIGS. 1 and 2, a visual stimulus can be provided on the video screen 24, optionally under the control of the central processing unit 7, or by manual control. The stimulus might for instance comprise a sequence of geometric shapes, or any suitable alternative for a particular application of the invention.

A stimulus such as a sinusoidal flicker, used to evoke an SSVEP, can then be superimposed by means of the goggles 4. This flicker can be generated under the overall control of the central processing unit 7, and as an electrical drive to the "led", by a frequency synthesizer 8 using a read only memory (ROM) look-up table for the sine form.

A reasonable frequency range within which a sinusoidal flicker stimulus might be selected might be 7 to 15 Hz, within which range cognitive effects have been found to be relatively prominent. In a particular embodiment, the stimulus might have a frequency of 13 Hz. This latter frequency has an advantage in that it lies in the aforementioned range, avoids the α frequency peak and thus avoids a reduced signal-to-noise ratio effect, and lies towards the high end of the range, this providing relatively quick analysis of a subject's response.

Preferably the amplitude of the flicker stimulus is ramped at start-up for the comfort of the subject 3, over a period of at least one minute. Feedback control is then provided by means of a branch 55 of the main optical fibre bundle 6 which divides off a small proportion of the light carried by the main bundle 6. This small proportion of light is fed to a light sensitive transistor 56 via a lens 57. The electrical output of the light sensitive transistor 56 is digitized and supplied to the central processing unit 7 which provides feedback control via the frequency synthesiser 8. The feedback control is used to maintain a linear relationship between a drive voltage supplied to the "led" 30 and the light intensity carried by the optical fibers 6, 6a, 6b.

Alternative apparatus for providing a flicker stimulus, by means of "leds" which provide light directly to the diffusers 29, is described in International application number PCT/AU86/00215 (WO 87/00746). Such an arrangement nay be adapted for use with optical fibers 6 as described above, the optical fibers 6 being inserted between the "leds" and the diffusers 29. The relevant description is therefore incorporated herein by reference. Again, overall control, such as start-up and amplitude adjustment, may be carried out by means of the central processing unit 7.

RESPONSE PICK-UP AND DATA ACQUISITION

Referring to FIGS. 1 to 5, brain electrical activity is recorded using silver/silver chloride electrodes 1 located at 64 scalp sites by means of the locators 11 and helmet bores 10. These sites are specifically indicated, in relation to the helmet 2, in FIG. 3 wherein solid rectangular electrode markers are used to indicate the sites of the international 10–20 electrode location system and open rectangular electrode markers are used to indicate additional sites, most of which are located substantially midway between the 10–20 locations.

The electrical connections 22 from the 64 electrodes 1 are collected into eight, 8-channel front-end differential amplifiers 31, which form the receiving end of the pre-processing block 9. These amplifiers 31 are of known type and monitor the signal output of the electrodes 1 by impedance. The output of each amplifier 31 is fed to a further processing unit 32, also of known type, comprising a bandpass filter, sample and hold circuitry, an analogue multiplexer and an A/D converter. The output of the A/D converter is then fed, still in real time, to a signal pre-processor 33 before being stored or further processed by the central processing unit 7.

Electrode impedance is tested by injecting a constant amplitude 40 Hz sinusoidal current of 1 nano amp into each electrode. The 40 Hz component is measured by the associated pre-processor 33 and is proportional to the electrode impedance.

Thus electrical brain responses detected by the electrodes 1 are pre-processed through eight, 8-channel paths in the pre-processing block 9.

Typically the amplifiers 31 might provide 20,000 times amplification, with a bandpass of substantially 0 to 30 KHz, for instance down 3 dB at 0.1 Hz and 30 Hz, being provided by the further processing unit 32. Sampling might be done at 16 or 32 samples per second and the analogue to digital conversion preferably provides an accuracy of 12 bits at a rate of 16 or 32 times the stimulus frequency.

SIGNAL PRE-PROCESSING

Figure 10:
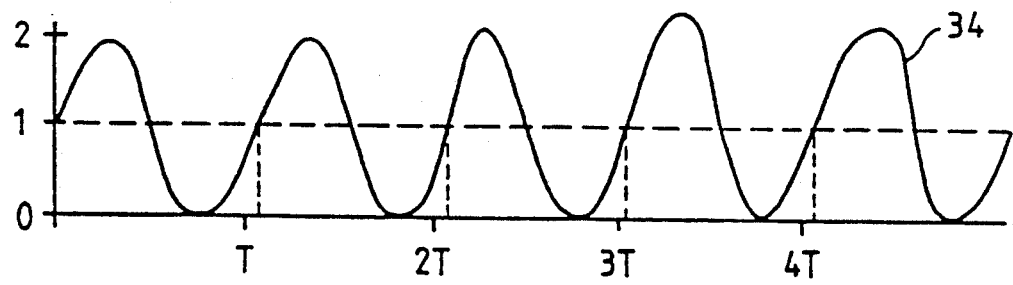
FIG. 10 shows the relationship between light intensity and time with regard to a flicker stimulus for use in the embodiments of the present invention.

The signal pre-processor 33 is provided so as to reduce the lead on the central processing unit 7. The signal pre-processor 33 itself may be microprocessor-based, Referring to FIG. 10, subjects are exposed to a visual sinusoidal flicker stimulus 34 at a specific frequency. Letting S(t) be the stimulus waveform, then $$S(t) = 1 + \sin \frac{2\pi t}{T} \quad (1)$$

The brain electrical activity V(t) as picked up by each electrode 1 is sampled at an interval $\Delta\tau$ such that $T/\Delta\tau$ is integral. As abovementioned, $T/\Delta\tau$ in the present case may be either 16 or 32.

Data is always sampled when $S(t)=1$.

It is this sampled data which is then fed to the pre-processor 33 where it is multiplied by a sine and a cosine waveform at the stimulus frequency and summed over the 16 (or 32) sample points to produce single cycle Fourier coefficients "$a_n$" and "$b_n$".

ie.

$$a_n = \frac{1}{16 \text{ or } 32} \sum_{J=\phi}^{J=15 \text{ or } 31} V(nT + J\Delta\tau)\sin 2\pi(nT + J\Delta\tau/T)$$

$$b_n = \frac{1}{16 \text{ or } 32} \sum_{J=\phi}^{J=15 \text{ or } 31} V(nT + J\Delta\tau)\cos 2\pi(nT + J\Delta\tau/T)$$

$$n = 0, 1, 2, \ldots, N - 1$$

The pre-processor 33 thus generates a string of "$a_n$" and "$b_n$" values. These are acquired by the central processing unit 7 which also acquires the V(t) sampled signal.

Figure 11:
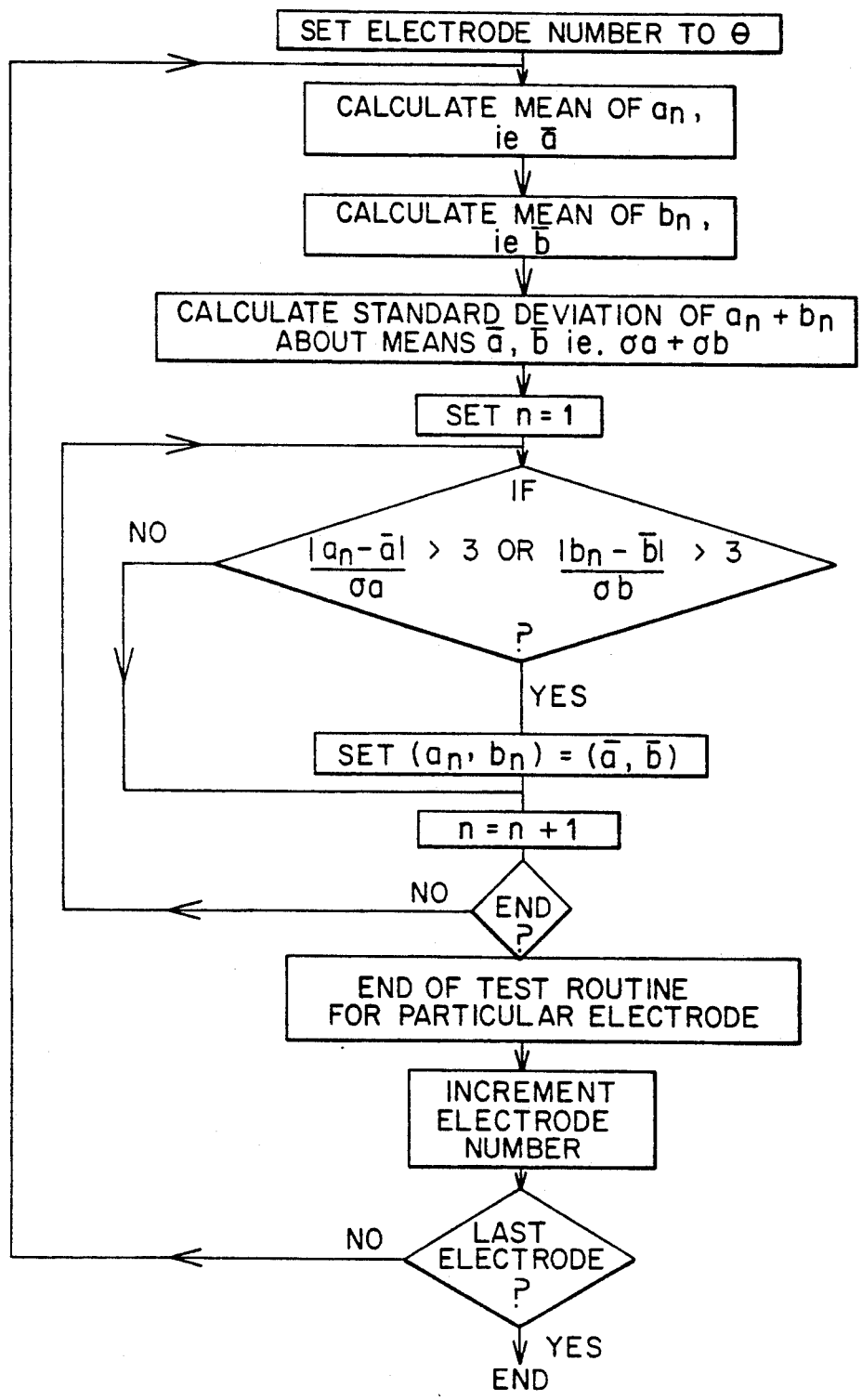
FIG. 11 shows a flow chart for use in testing single cycle Fourier coefficients, generated during signal processing, for anomolous values.

Under certain circumstances, artifacts due to blinks, eye movements, body movements etc, can cause an anomolously large "$a_n$" or "$b_n$" to be generated. An algorithm which tests each pair of $a_n$ and $b_n$ for anomolously large values is then employed. Referring to FIG. 11, the operation of the algorithm is clear from the associated flow diagram. It merely checks "$a_n$" and "$b_n$" for each electrode 1 against the average of all "$a_n$, $b_n$" values for that electrode, and replaces any which is too high, that is by more than three times the standard deviation, with the relevant average value.

The output of each pre-processor 33 can then be stored, or supplied via an optical isolator 34 to the central processing unit 7. Here, further analysis is carried out, prior to data display and storage.

MAIN DATA PROCESSING, DISPLAY AND ANALYSIS

A first, protective function of the central processing unit 7 is to detect possible epileptic activity of a subject 3. To do this, the detected mean values of $a_n$, $b_n$ are compared with a predetermined threshold. If this threshold is exceeded for a given time, the subject 3 is deemed to be experiencing epileptic activity and the amplitude of the flicker stimulus is set to zero.

The central processing unit 7, in carrying out further analysis next generates a magnitude time series by calculating a "moving average" of the single cycle Fourier coefficients over a plurality of cycles, or recording phase. To calculate the moving average, the following sum can be performed:

$$\tilde{a}_n \equiv \frac{1}{W} \sum_{J=\phi}^{J=W-1} a_{n+J}$$

$$\tilde{b}_n \equiv \frac{1}{W} \sum_{J=\phi}^{J=W-1} b_{n+J}$$

W being integral and typically in excess of 50.

In an alternative approach, the moving average can be calculated with a specific weighting applied to each of the $a_n$ and $b_n$ values, as follows:

$$\tilde{a}_n = \sum_{J=\phi}^{J=W-1} g(J)a_{n+J}$$

$$\tilde{b}_n = \sum_{J=\phi}^{J=W-1} g(J)b_{n+J}$$

where $g(J) = \frac{1}{W}(1 + \cos(2\pi J/W - \pi))$

An un-normalised magnitude time series can then be defined by $$M_n = \sqrt{(\tilde{a}_n)^2 + (\tilde{b}_n)^2}$$

and a phase $\theta_n = \text{Tan}^{-1}(\tilde{a}_n/\tilde{b}_n)$ where, $-\pi/2 \leq \theta_n \leq \pi/2$. For values of $\theta_n$ outside this range the standard forumulae can be used for calculation of $\theta_n$.

As $M_n$ is defined at specific time intervals, the subscript can be dropped, i.e.:

$M(t) = M_n$ where t is time.

For a given task (x), subjects s and electrode e can be written:

| M(t) e, s, x | |
|---|---|
| e = No of electrode, | ie 0, 1, . . . , 63 |
| s = subject No. | ie 0, 1, 2, . . . S |
| x = task numbers | ie 0, 1, . . . X |

Significantly in embodiments of the present invention, reductions in M(t) indicate increased regional brain activity, e.g. as a result of a subject 3 reacting in a particular manner to material displayed on the video screen 24.

The central processing unit 7 thus generates 64 separate time series, one for each electrode site, for a single recording phase.

A valuable of primary application of embodiments of the present invention is to compare results between different subjects 3. To compare populations, it is generally necessary to average the responses of different subjects. Two factors must however, be taken into account prior to averaging.

1. There are very large magnitude differences between subjects, and
2. The average phase $\theta$ will also widely differ from subject to subject.

To compensate for 1, a normalization factor is calculated. Normalisation is achieved by calculating the mean magnitude recorded at each electrode site during a viewing phase and then averaging the 64 values for each subject. This yields a single value for each subject representative of the mean magnitude of the SSVEP during viewing. The individual Fourier coefficient time series are then divided by this normalisatton factor prior to cross subject averaging or other multiple subject data processing. Failure to carry out this normalisation could lead to a "skewing" of results by the larger SSVEP's.

Advantageously, synchronization is provided between the frequency synthesiser 8 and the sample and hold circuitry of the further processing unit 32, by means of the central processing unit 7. That is, the sampling rate is effectively controlled by the frequency synthesizer 8. This streamlines data pre-processing since the phase relationship $\theta$ between stimulus and response becomes a function of the stimulus frequency and the delay between the stimulus and response (i.e. the latency of the response).

There can be large intersubject variations in latency. These variations would lead to at least part cancellation of responses when vector averaging is performed across a subject pool. When cross subject averaging, the latency of the response is not of interest, the primary concern being with amplitude variations.

Phase rotation permits cross subject averaging without partial cancellation of the responses. In addition, as a separate matter, variations in phase occurring during the recording session can be preserved for further analysis.

To compensate for 2, the average phase of each time series is evaluated and the phase of each pair of points (i.e. $a_n$, $b_n$) is rotated by minus the average phase. This yields a new average phase of zero. These normalised, phase rotated time series of $(a_n, b_n)$ can now be averaged as a complex series.

The central processing unit 7 controls a visual display unit 35 (not shown on FIG. 1) to put up maps of evoked brain activity in response to changing stimuli, detected in terms of the SSVEP. Hence a spatio-temporal distribution of evoked activity can be evaluated while the subject 3 is performing a range of cognitive tasks intended to activate patterns of brain activity with diagnostic value.

The 64 M(t) values for a particular instant of time, particular subject and cognitive task can be mapped by interpolating additional points, typically 64,000, and then colour coding. Displays so generated are shown in FIGS. 15 to 17. Interpolation techniques which might be used in this respect are known and although one particular technique is referenced below in the presentation of a practical experiment applying an embodiment of the present invention, other techniques might be substituted.

An option with respect to information to be mapped is to display differences in brain activity associated with different tasks. For example, where the task numbers x=3 and 5, a map can be based on the 64 values of (M(t) $\theta$, s, 3 —M(t) e, s, 5).

It should be noted that although the central processing unit 7 is described above with reference to putting up maps of brain activity on a visual display unit 35, in practice a great range of information, in different forms, may be output by the unit 7, this depending at least in part on the sophistication of the unit 7, including its available memory. A variety of outputs 26 may also be available, these being indicated on FIG. 2 and including for example outputs to a mathematics co-processor, streaming tape backup, ink jet printer for hard copy, laser jet printer, and/or a plotter.

Control of the central processing unit 7, for instance in terms of parameters to be applied in data analysis, outputs to be selected, or data analysis tasks to be performed, can simply be input by conventional input means 53 such as a light pen, mouse, and/or a keyboard.

Further, although as described above the signal pre-processor 33 merely generates "$a_n$" and "$b_n$" values, and checks these for artifacts, the division of operations between the pre-processor 37 and the central processing unit 7 could be changed, for instance where the capacity of the pre-processor 33 is selected to be greater. Thus the central processing unit 7 could have improved capacity for data processing if the pre-processor 33 carries out additional preliminary tasks. These might include for instance calculation of the magnitude time series, M(t).

In order to show more fully the operation and application of an embodiment of the invention substantially as described above, an experiment together with displays and results will now be described.

EXPERIMENT; PROCEDURE

Referring to an application of an embodiment of the present invention, as mentioned above, the basic premise underlying the Probe-ERP paradigm is that regional increases in cortical activity associated with the cognitive processes will, in turn, give rise to smaller potentials evoked by an irrelevant (or Probe) stimulus (Papanicolaou & Johnstone 1984).

In embodiments of the present invention, the Probe-ERP paradigm is combined with the SSVEP to investigate the effects of a prolonged visual attention task on the time course and topography of the SSVEP. It was thought that the combination of high spatial resolution, short Fourier integration period and the Probe-ERP technique would maximize the possibility of observing SSVEP changes associated with cognitive processes. This technique will be subsequently referred to as Steady-state Probe Topography (SSPT). As a demonstration of SSPT, changes in the SSVEP topography associated with a visual vigilance task were considered. A vigilance task was selected because it was thought to lend itself well to the investigation of electrophysiological indicators of time varying cognitive processes.

In a particular application, subjects 3 were required to view a series of 180 geometrical shapes over a period of 180 seconds while fixating on the centre of the screen 24. The shapes were presented three times during the experiment. In the first and second viewings, subjects were given no specific instructions while prior to the third viewing, they were instructed to identify a modification applied to one of the circles. Successful identification of the modification was rewarded financially. It was reasoned that the subjects 3 would be in higher state of visual attentiveness during the third viewing when compared with the second. The first viewing was used to familiarize subjects with the experimental protocol and reduce any novelty effects.

In designing this experiment, the possible effect of variations in gaze position on the SSVEP topography was also considered. Changes in the retinal position of small patterned transient stimuli have been shown to affect occipital ERP topography (Halliday et al 1977). It is therefore conceivable that differences in the pattern of small eye movements could lead to differences in the average direction of gaze relative to the target. This may occur in spite of the instruction to all subjects to maintain their fixation point on the centre of the screen. These possible differences in gaze position could in turn affect the SSVEP topography and thus confound any cognitive effects on the SSVEP.

To assess the importance of this effect, a preliminary experiment was under taken in which SSVEP measurements were recorded at 64 scalp sites while subjects systematically varied their gaze position relative to the target. Further details of this preliminary experiment are given below, under the heading "DISCUSSION OF EXPERIMENT AND RESULTS".

Principally, it was hypothesized that cortical regions with increased neural activity associated with the task would demonstrate an attenuated SSVEP. More specifically, it was expected the occipito/parietal regions, known to mediate visual processes (Poggio 1980), would show an attenuation of the SSVEP during and after the viewing of the "target" circle.

Subjects: 15 right handed males with normal uncorrected visual acuity served as subjects. Handedness was assessed using the Edinburgh inventory (Oldfield 1971) and visual acuity using a Snellen chart. The age of the subjects ranged from 18 to 42 (mean 24.1 sd 6.3). All subjects gave their informed consent prior to participating in the study.

Four additional subjects satisfying the above selection criteria were involved in the preliminary experiment.

Tasks

Subjects were requested to fixate on the centre of a video screen and observe a sequence of geometrical shapes presented there. The sequence consisted of series of 60 squares followed by 60 circles followed by another 60 squares. A shape appeared on the screen every second and was displayed for a period of 500 msec. During the 500 msec that neither a circle or square was present, a cross was displayed in the centre of the screen to serve as a fixation point.

Figure 18:
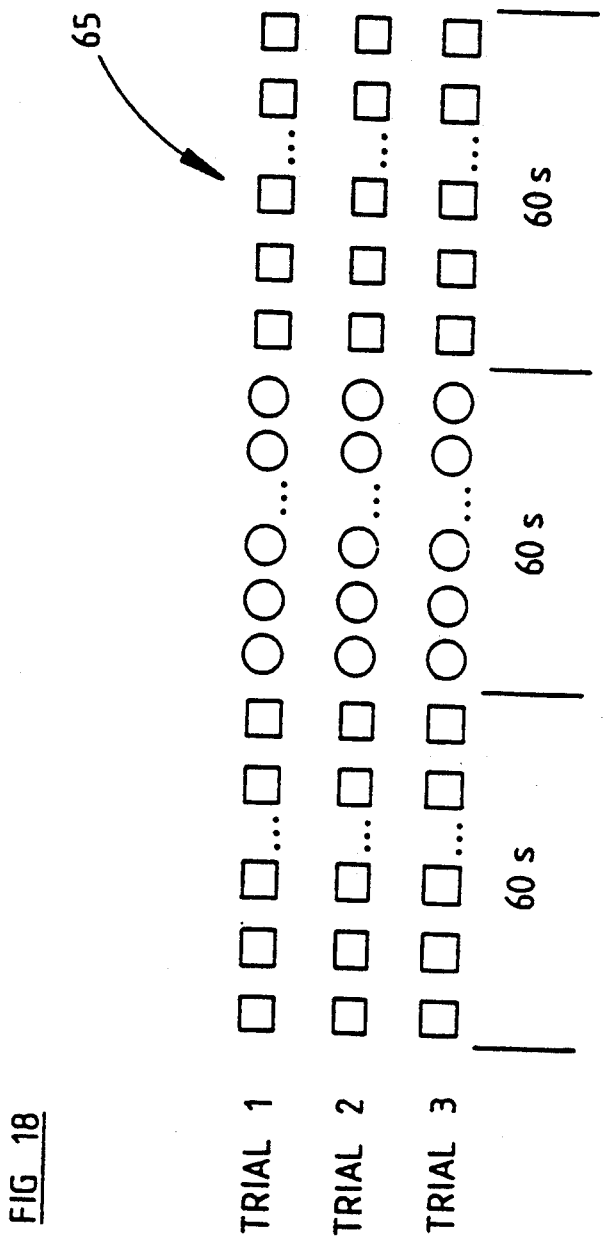
FIG. 18 shows an experimental protocol.

Referring to FIG. 18, subjects were requested to view the sequence 65 of 180 shapes three times, each of the three viewings constituting a trial. During the first and second viewings, the subjects were simply requested to fixate on the centre of the screen and observe the sequence of shapes. During the third viewing, subjects were requested to attend to a modification that had been applied to the last of the circles in the third sequence and were informed that successful identification would be financially rewarded. Prior to the completion of the third viewing, subjects were naive as to which circle had been modified or the nature of the modification.

Trial one was used to familiarize the subjects with the task, trial two was a passive viewing task while trial three was an active viewing task characterized by increased attentiveness.

To verify task performance, subjects were requested to identify the nature of the modification at the end of the third viewing. This was done by displaying nine circles, each with a different modification, and requiring subjects to select the modification presented in the third trial. Results obtained during the first viewing were disregarded as this was used to familiarise the subjects with the experimental procedure and environment.

In addition, 180 seconds of brain activity was also recorded in the absence of the sinusoidal visual stimulus. This was used to estimate the level of background activity in the recording. During this "no stimulus" phase, subjects were required to fixate on the central cross for 180 seconds.

During the preliminary experiment, a cross identical to the one used in the main experiment was presented on the centre of the monitor for a period of thirty seconds. During this period, subjects were required to fixate on one of three possible screen positions for thirty seconds. These three positions comprised the central cross and two identical crosses located 12° to the left and right of the central cross. Subjects were required to view each of these positions eight times making a total of twenty four viewings for each subject.

Stimulus

Each of the geometrical shapes and the central fixation point in the form of a cross subtended an angle of 1° vertically and horizontally when viewed by the subject at a fixed distance of 1.0 m. All shapes were presented at the central fixation point.

The shapes had an illuminance of 13.0 Candela per square meter ($Cd/m^2$) against a screen background of 1.2 $Cd/m^2$.

The stimulus used to evoke the SSVEP consisted of a superimposed 13 Hz sinusoidal flicker stimulus subtending a horizontal angle of 80° and a vertical angle of 30°. The maximum illuminance associated with the peak of the stimulus waveform was 3.2 $Cd/m^2$ and the minimum, when viewed against the background was 1.2 $Cd/m^2$. The modulation depth was therefore 45%.

Recording

The optimum number of recording sites to adequately sample the scalp distribution is determined by the spatial variability of the recorded signal. The relationship between this spatial variability and the maximum inter-electrode distance is given by the Nyquist criterion which indicates that the spatial sampling frequency must be more than twice the spatial bandwidth of the signal (Spitzer et al 1989). The minimum spatial sampling frequency (or its inverse, the maximum inter-electrode separation) is thus determined by the spatial bandwidth of the electrophysiological signal being recorded. Gevins (1986) quotes a minimum spacing of 2 cm to adequately sample a visually evoked potential generated by an unstructured visual stimulus while Spitzer et al (1989) indicate that a strict application of the Nyquist criterion for somatosensory ERPs necessitates a maximum inter-electrode spacing of 1.5–1.8 cm. They suggest that it is appropriate to relax this criterion and recommend a maximum spacing of 2.9 cm. The number of recording sites in the current study was 64. This yielded an average inter-electrode separation of 3.2 cm. while larger than the 2 cm recommended by Gevins, this inter-electrode separation significantly reduces the possibility of missing some of the smaller topographic features.

Figure 3:
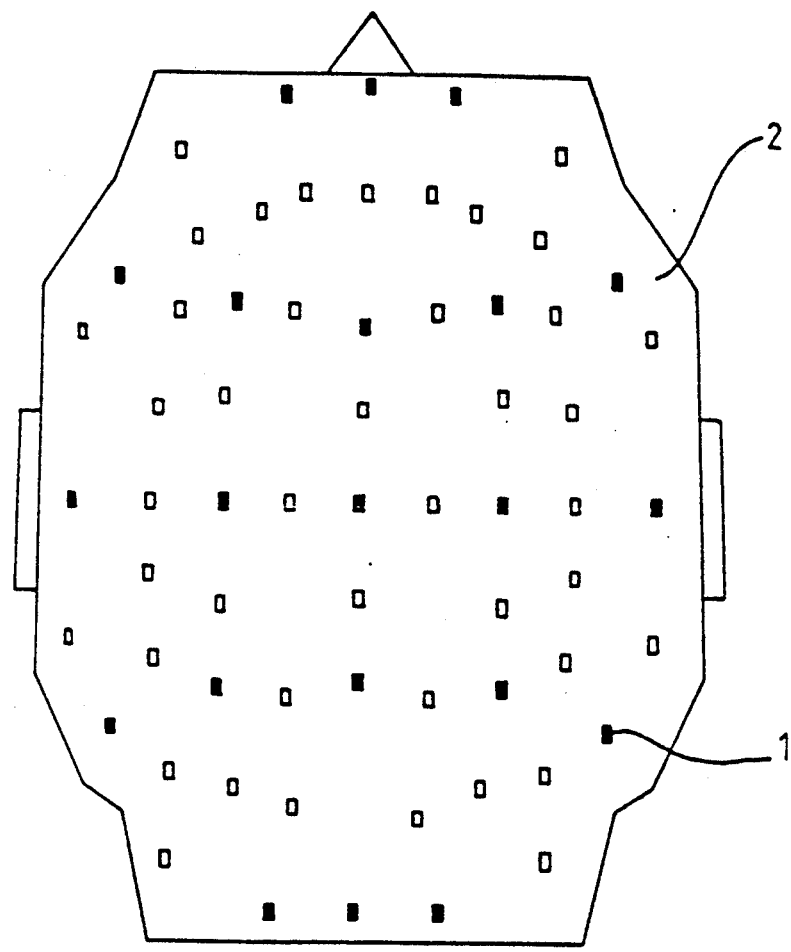
FIG. 3 shows a schematic plan view of electrode sites on the head of a subject of tests according to an embodiment of the present invention.

Brain electrical activity was recorded using silver/silver chloride electrodes located at 64 scalp sites. The recording locations included all the scalp positions in the international 10-20 System with additional sites located midway between the 10-20 locations. These locations are illustrated in FIG. 3.

All recordings were referenced to linked ear lobes with forehead serving as ground. Brain electrical activity was amplified 20,000 times with a bandpass down 3 dB at O.1 Hz and 30 Hz. Date was then digitized to 12 bit accuracy at a rate of 200 Hz and stored on hard disk for subsequent off-line analysis. All stimulus control, data acquisition and signal processing was performed using an AT compatible computer (Schist et al 1988).

Prior to viewing 1; 180 seconds of brain activity was recorded from all 64 sites in the absence of the sinusoidal visual stimulus. During this "no stimulus" phase, subjects were required to fixate on a square located in the centre of the screen for 180 seconds.

Signal Processing

The magnitude time series M(t) is then calculated according to the method described above under the headings "SIGNAL PRE-PROCESSING" and "MAIN DATA PROCESSING, DISPLAY AND ANALYSIS". Alternatively, in a computationally slower manner, the magnitude of the 13 Hz component can be determined by firstly evaluating the cosine and sine 13 Hz Fourier coefficients over the initial 10 seconds of recording phase. The duration over which the SSVEP is evaluated is a compromise between noise rejection and the capacity to follow rapid changes in the SSVEP magnitude. The Fourier analyser can be considered as a band pass filter centred on the stimulus frequency. The bandwidth of this filter is inversely proportional to the integration period used in the Fourier analyser. Longer integration periods will therefore reject more of the brain electrical activity not centred on the stimulus frequency and consequently increase the signal to noise ratio. Another effect of increasing the integration period is a reduced capacity to follow changes in the SSVEP magnitude. This is a consequence of the integration procedure acting as a low pass filter (Regan 1989). The 10 second integration period selected permitted a consideration of SSVEP magnitude changes having a time course larger than 10 seconds while yielding adequate rejection of EEG components unrelated to the stimulus.

The magnitude of the Fourier coefficients is calculated by taking the square root of the sum of the squares of the Fourier coefficients. The 10 second period over which the Fourier coefficients are evaluated is then shifted one cycle of the stimulus (i.e. 1/13th of a second) and the magnitude recalculated for this overlapping period. This process is continued until the entire 180 second segment has been analyzed.

This procedure yields an SSVEP magnitude time series 170 seconds (i.e. 180 seconds minus the 10 second evaluation period) in duration.

An identical procedure can be applied to data recorded from all 64 recording sites.

The focus of this study concerned the changes in the magnitude of the SSVEP associated with an attention task. For this reason, the SSVEP phase information (which can also be derived from the Fourier coefficients) was not used.

The data from each subject then yielded 64 separate times series for each trial. Group data for each trial were represented by 64 magnitude time series formed from a cross subject average of the Fourier coefficient time series. Fourier coefficients for a given electrode and trial were separately averaged and the magnitudes of the Fourier coefficients calculated. As there are large variations in the absolute magnitude of the SSVEP across subjects, a feature reported by Klemm (Klemm et-al 1980), the normalised Fourier coefficients were used to form the cross subject average. Normalisation was achieved by calculating the mean of the magnitude time series associated with trial two. These 64 values (one for each electrode) were then averaged to yield a single value for each subject. This value became the normalisation factor for the subject. The individual Fourier coefficient time series for trials 2 and 3 for each subject were then divided by the subjects' specific normalization factor prior to cross subject averaging. Failure to carry out this normalisation could lead to a skewing of the cross subject average by the larger SSVEPs. The magnitude time series of the group data were then represented as a multiple of the mean value during trial 2.

To examine the differences between trial 2 and 3, the Students' t-parameter, based on a paired t-test was evaluated for each point in the magnitude time series at each electrode. This yielded 64 distinct t-parameter time series, i.e. one Students' t-parameter for each corresponding point in the normalised SSVEP magnitude time series in trials 2 and 3. This t-parameter gave an estimation of the statistical strength of the effect. In addition to the Students' t-parameter being evaluated, the difference between normalised magnitude time series for trials 2 and 3 was also calculated.

In the preliminary experiment, the magnitude of the 13 Hz component was calculated using a 30 second integration period. The 30 second integration period was used because it corresponded to the time that subjects fixated on one of the three video monitor positions. For each subject, this yielded one magnitude measure at every recording site for each of the 24 viewings (i.e. 3 positions repeated 8 times). Normalisation of these measures was achieved by calculating the mean magnitude over the 64 recording sites and 24 viewings (i.e. 1536 values) for each subject and dividing the magnitudes by this value.

Topographic mapping

Topographic maps of the differences between viewings (trials) 2 and 3 normalised magnitude time series, as well as the Student's t-parameter time series associated with each of the 64 recording sites, were produced using a two dimensional quadratic surface interpolation procedure similar to that described by Dubinsky and Barlow (1980). The quadratic surface was derived from the values of the magnitude difference or the Student's t-parameter at the six recording sites nearest the interpolating point. Smoothing of the interpolating values was then performed to reduce discontinuities at adjacent interpolating surfaces. This was carried out by replacing each point with the average of a $9 \times 9$ (81) array of interpolated values centred on the point in question. The 32000 interpolated values produced by the interpolation procedure were displayed using a range of 256 graded colours. This range of colours avoided the appearance of discontinuities in the map which can occur at the boundaries of dissimilar colours.

Maps of the difference between trials 2 and 3 will be referred to as difference maps while maps of the Students' t-parameter will be referred to as t-parameter maps. Those parts of the difference maps where the difference between trials 2 and 3 were zero were coloured black. This enabled rapid identification of the regions showing no inter-trial changes. A similar procedure was applied to the maps of the Students' t-parameter. In this case, regions where t values equal to 1.76 or 2.97 were coloured black. These values correspond to probability values of 0.05 and 0.005 in a one tailed t-test with 14 degrees of freedom. Values for a one tailed rather than a two tailed test were illustrated as the hypothesis was that SSVEP magnitudes would be reduced in trial 3 compared to trial 2.

EXPERIMENT: RESULTS

The preliminary experiment was analysed by performing a single factor, repeated measures analysis of variance (ANOVA) at each of the recording sites using a statistical package such as MINITAB V7.1. (This latter is a package available for use on an IBM personal computer, or compatible equipment.) The results indicated that gaze position had no statistically significant effect on the SSVEP magnitude recorded at any of the 64 sites. F values ranged from a minimum of $F(3,2)=0.06$ ($p=0.94$) at electrode 8 to a maximum of $F(3,2)=2.6$ ($p=0.15$) at electrode 48.

All subjects successfully identified the modification of the circle in the main experiment.

A comparison of viewings two and three indicated that the appearance of the modified circle was associated with an attenuation of the SSVEP in the occipito-/parietal region. The same comparison indicated a pronounced SSVEP attenuation in the centro/parietal region during the interval that subjects were anticipating the appearance of the modified circle. These results suggest a distinction between the cortical activation patterns occurring during different phases of a visual vigilance task.

Figure 12:
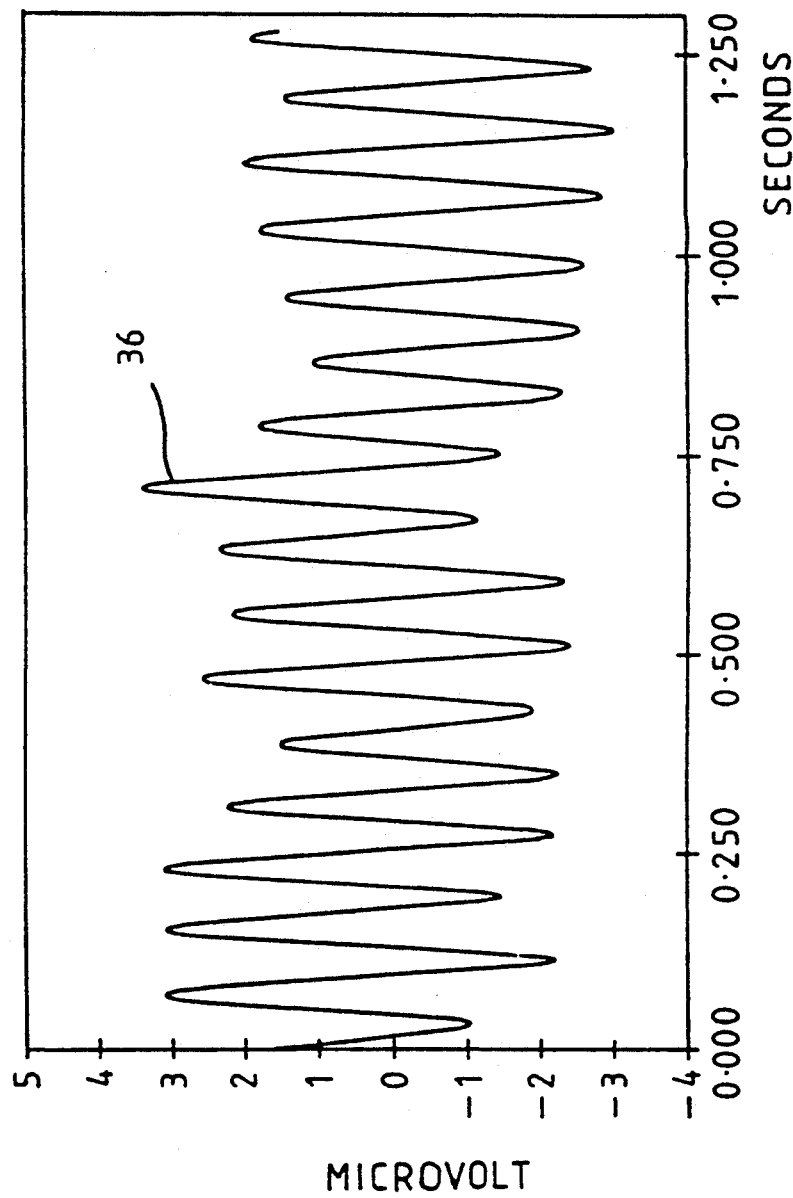
FIG. 12 shows the sinusoidal nature of an SSVEP after conventional averaging.

Referring to FIG. 12, the sinusoidal feature of the SSVEP can be seen for the case where conventional averaging, synchronized with a fixed point in the stimulus cycle, is employed. This Figure shows the averaged evoked potential 36 recorded from a single subject (CD) during viewing 2. This conventional average of 120 sweeps of activity recorded from position Oz (electrode 61) clearly shows the sinusoidal feature of the response.

Referring to FIG. 13A, this Figure shows the SSVEP magnitude time series 37 recorded from a single subject (subject CD), associated with trials 2 and 3, at electrode 38 located midway between P3 and C3. That is, at the left parietal site.

Figure 13B:
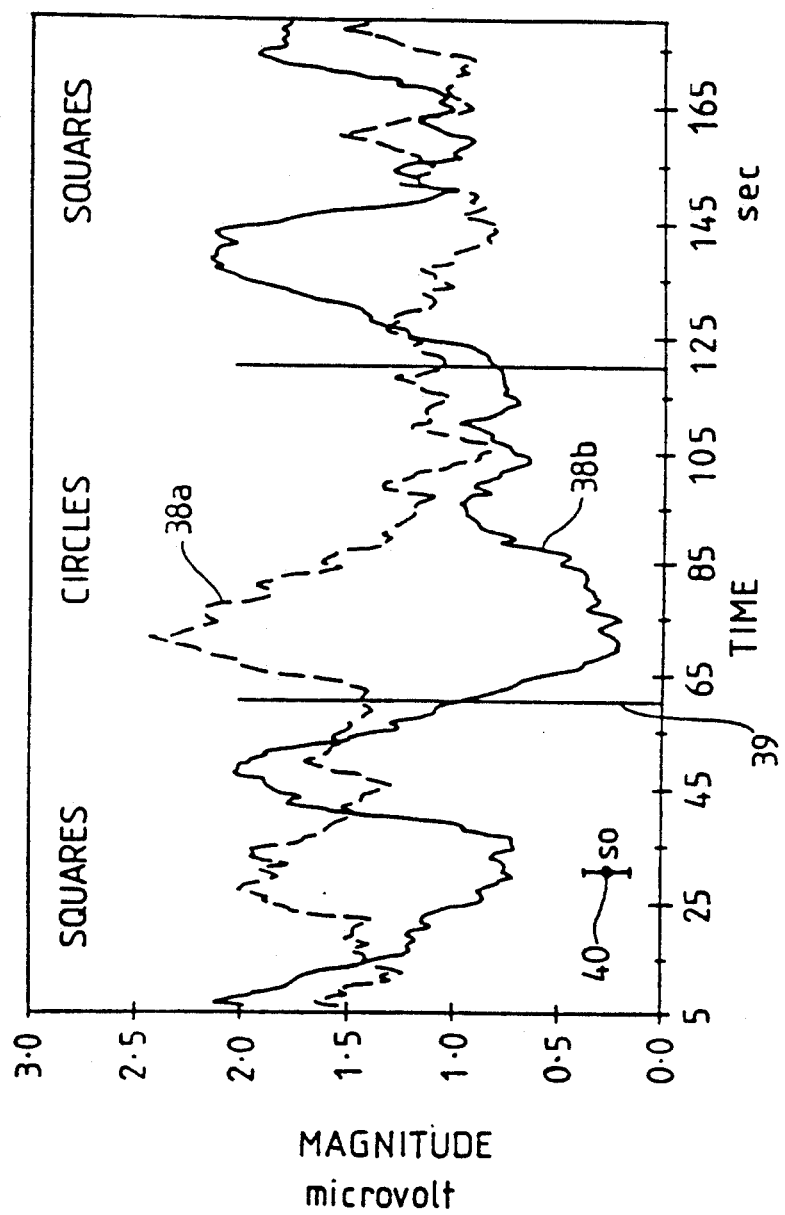

FIG. 13B is the comparable times series 38 for the contralateral recording site at electrode 42.

The broken lines 37a, 38a illustrate the activity during viewing 2 while the solid lines 37b, 38b relate to viewing 3. The period from the start of the sweep to the first of the vertical bars 39 corresponds to the first sequence of 60 squares. The second and third intervals correspond to the circles and squares respectively. The single data point 40 labelled "so" represents the mean SSVEP magnitude recorded in the absence of a sinusoidal stimulus. This gives an indication of the magnitude of the spontaneous 13 Hz activity and could be considered the noise level. The error bars on the point represent one standard deviation of the stimulus-off response.

All plots in FIGS. 13A and 13B show large fluctuations. These are similar to the auditory steady state potential fluctuations reported by Galambos and Makeig (1988).

Figure 14A:
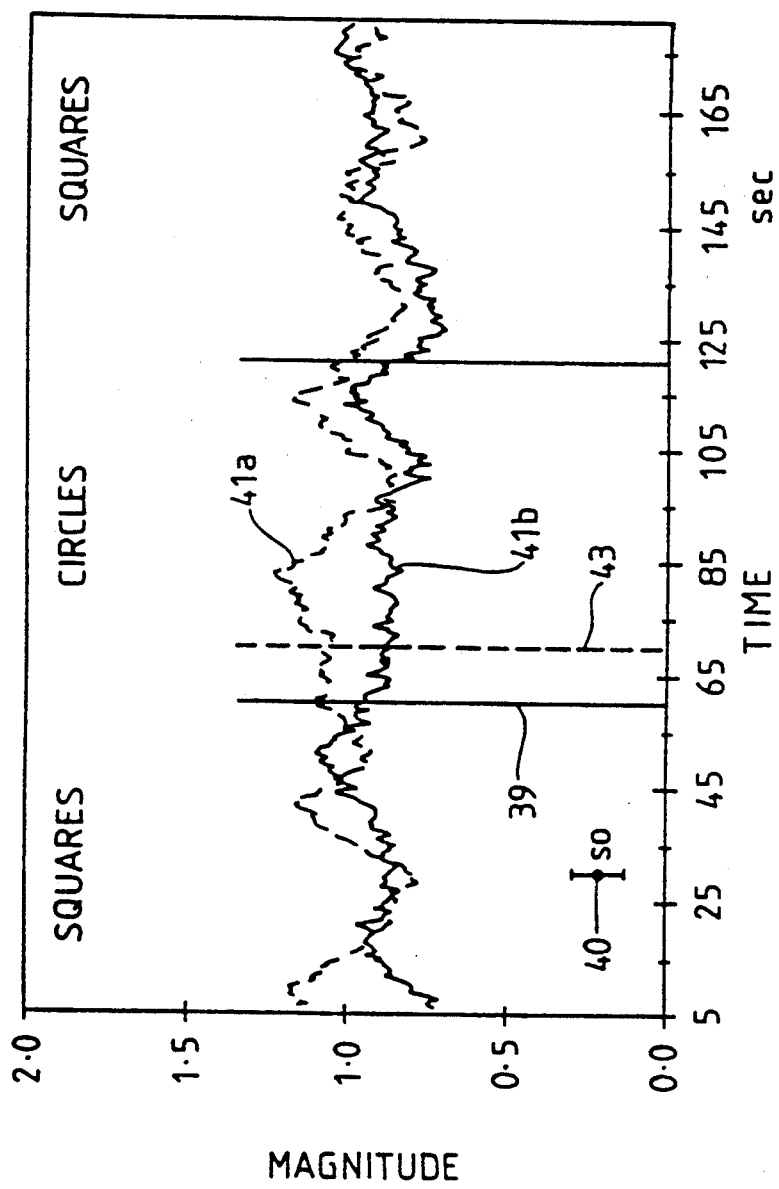
FIGS. 14a and 14b show magnitude time series results for a cross subject average measured at two different electrode sites.
Figure 14B:
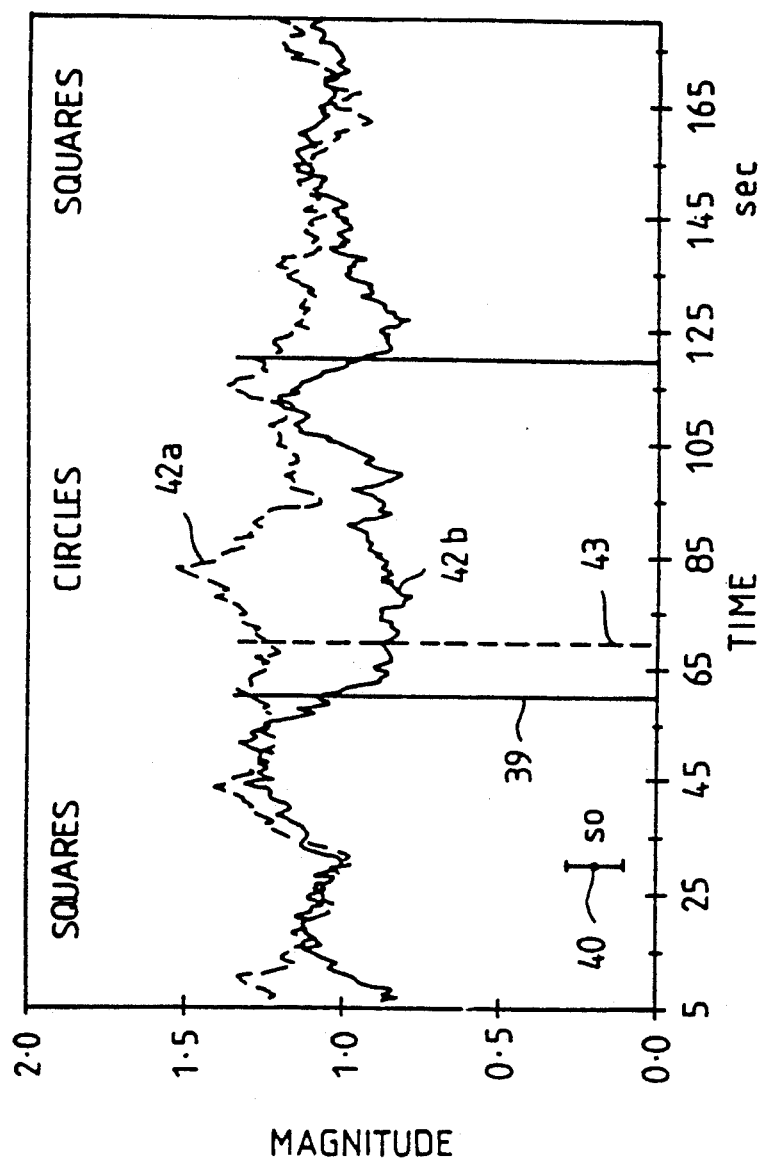

FIGS. 14A and 14B illustrates the magnitude time series 41, 42 of the cross subject average recorded from the same electrode sites (38 and 42) as FIGS. 13A and 13B. That is, FIG. 14A refers to the left parieto central region recorded from electrode No. 38 while FIG. 14B illustrates the equivalent activity from the contralateral recording site at electrode No. 42. Again, the broken lines 41a, 42a relate to viewing 2 while the solid lines 41b, 42b relate to viewing 3. The dotted vertical line 43 indicates the time at which the "anticipation" phase was evaluated. Note, the units on the vertical axis are given in terms of normalized magnitude.

These plots illustrate the variations in the SSVEP magnitude normalised with respect to the mean value of trial 2. During the presentation of the circles, the SSVEP magnitude was reduced in trial 3 compared to trial 2. This effect was apparent at the parietal and occipital sites.

To render the presentation of the results more tractable, only three points in the trials were considered. The first coincided with the appearance of the first circle in trials 2 and 3. The first circle in trial 3 alerted the subjects to the possible appearance of the modified circle and thus constituted the signal for subjects to heighten their attentiveness to the video monitor. Another point in the trials to be considered is the one coinciding with the appearance of the last or target circle. In trial 3 this was the instant of target detection, the culminating task set for subjects in this experiment. These two points were thus considered as logical foci for further consideration. In the 60 seconds between the appearance of the first and the target (last) circle, the subjects were presumably in a state of anticipation awaiting the target circle. This presumed state of anticipation coincided with a prolonged reduction of the trial 3 SSVEP magnitude when compared with trial 2. This trial 3 SSVEP reduction was diffusely distributed in the occipital/parietal region and peaked approximately 10 seconds after the appearance of the circles. It subsequently decayed over the following 50 seconds. During this 50 second decay phase, the topography of this attenuation was essentially unchanged. The point in time coinciding with its maximum (10 seconds after the appearance of the circles) was thus selected as representative and constituted the third point for further consideration. In the subsequent discussion of the results, the point coinciding with the appearance of the circles will be termed "presentation", the point 10 seconds later will be termed "anticipation" while the appearance of the target circle will be termed "detection".

Three separate Analyses of Variance, using MINITAB V7.1 were undertaken to assess the differences between trials 2 and 3 at the times of presentation, anticipation and detection. A three factor repeated measures design for main effects and all second order interactions was used. These factors were trials (2), subjects (15) and electrodes (64). Regional differences in the viewing effects are reflected in the viewing X electrode interaction terms. While this term did not reach significance at the 0.005 level for the cueing phase, (dF(63,882), F=0.37, p>0.95) it reached significance at the anticipation (F=1.51, p<0.005) and detection phases (F=2.28, p<0.0005)

Figure 19B:
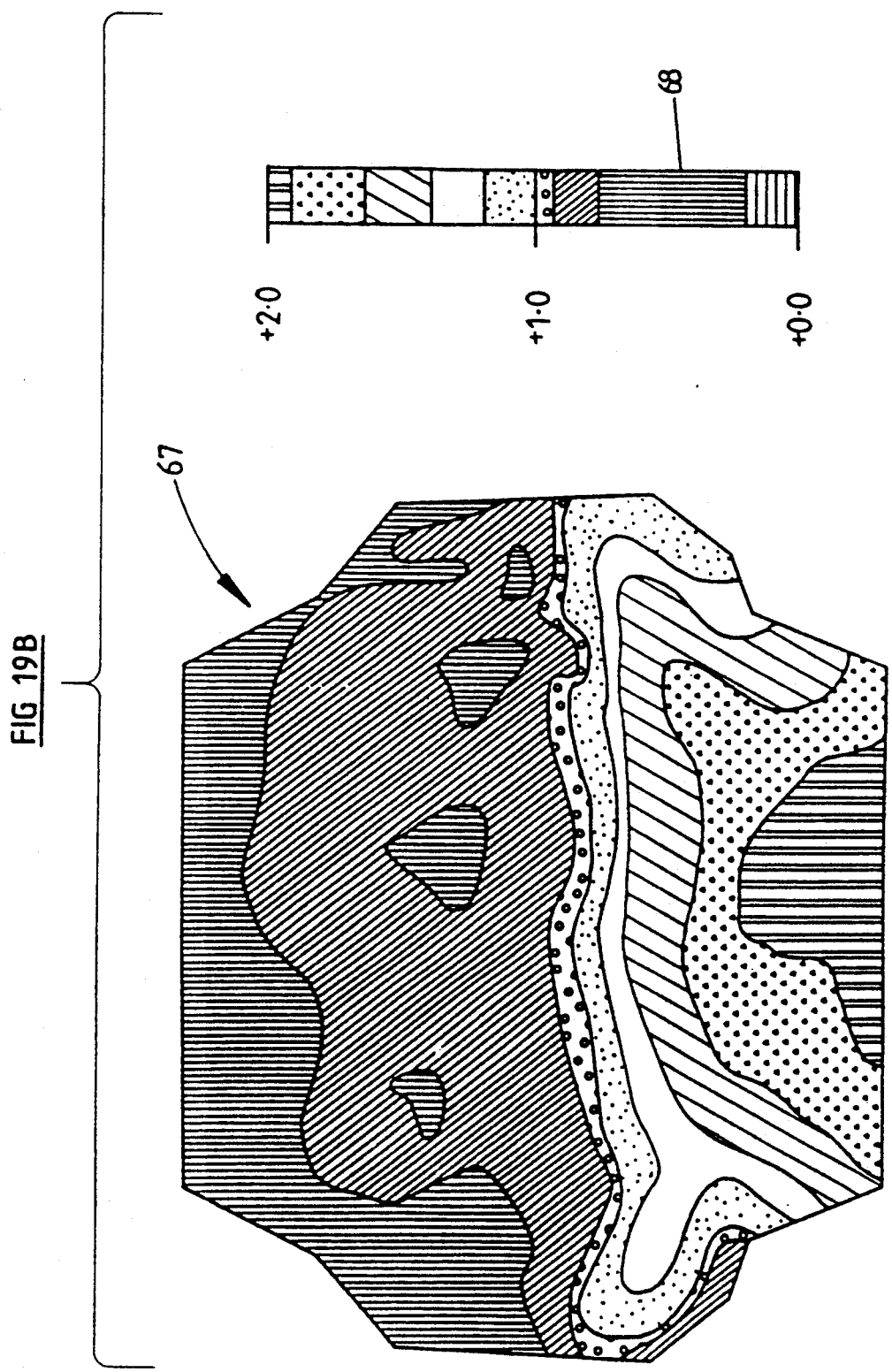

Referring to FIGS. 19A and 19B, FIG. 19A, illustrates the topographical distribution 66 of the cross subject averaged SSVEP magnitude at the appearance of the circles in trial 2. FIG. 19B is the equivalent illustration 67 for the appearance of the circles in trial 3 when subjects have been alerted to the appearance of a modified circle. The diffuse SSVEP maxima seen in the occipito/parietal regions of FIGS. 19A and 19B have been previously reported (Silberstein et al 1988).

It should be noted that the zones of each of FIGS. 15A and 15B, 16A and 16B, and 17A and 17B and 19A and 19B are in practice distinguished by colour, this being represented in the Figures by different markings. Each Figure has an accompanying "colour bar" 47, 68 to identify the zones.

Figure 15A:
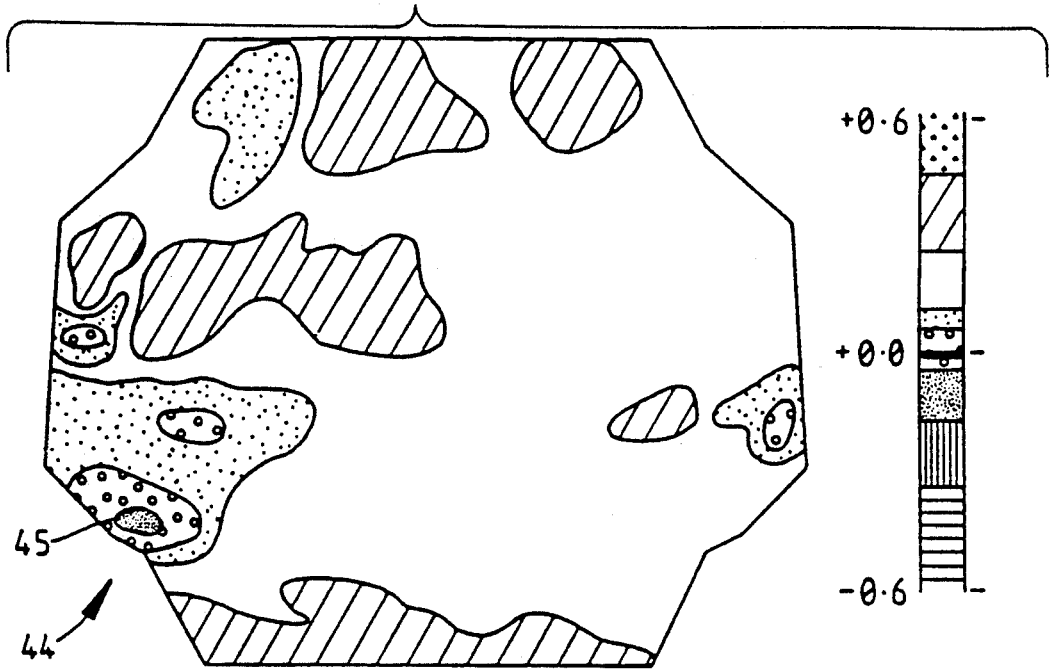
FIGS. 15a and 15b show a comparison of the topographic distribution of results for a subject under different viewing conditions.
Figure 16A:
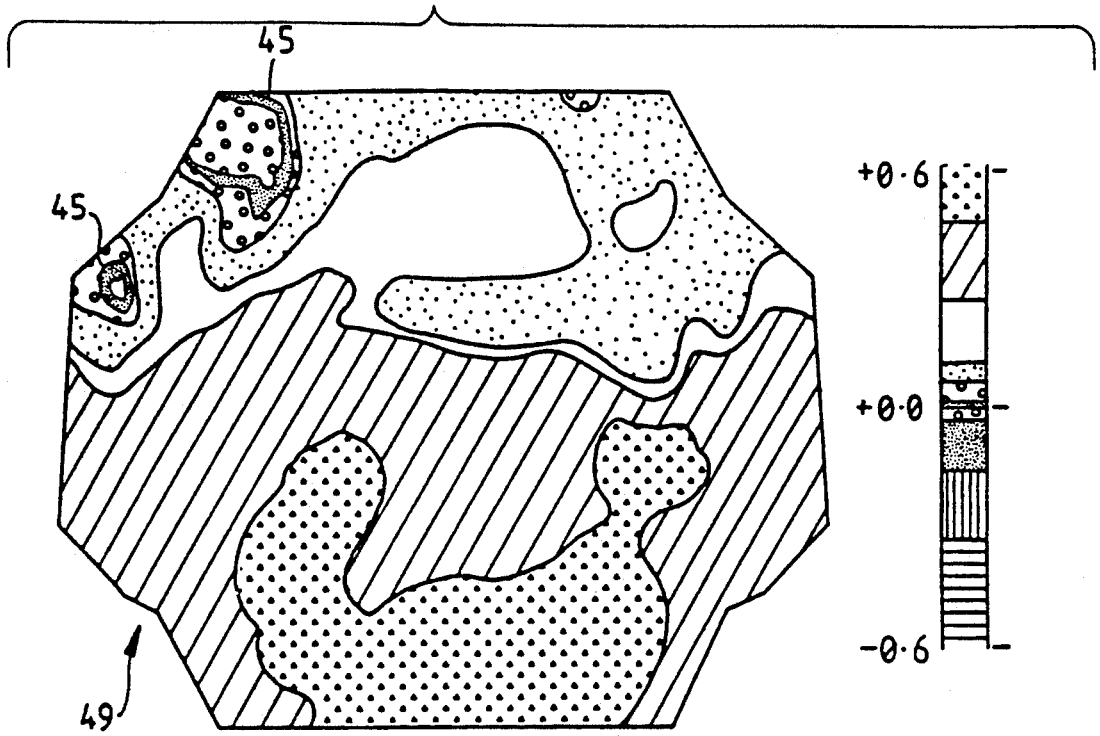
FIGS. 16a and 16b shows differences in a topographic distribution of results for a subject under different viewing conditions, and the distribution of a corresponding Students - t parameter.
Figure 16B:
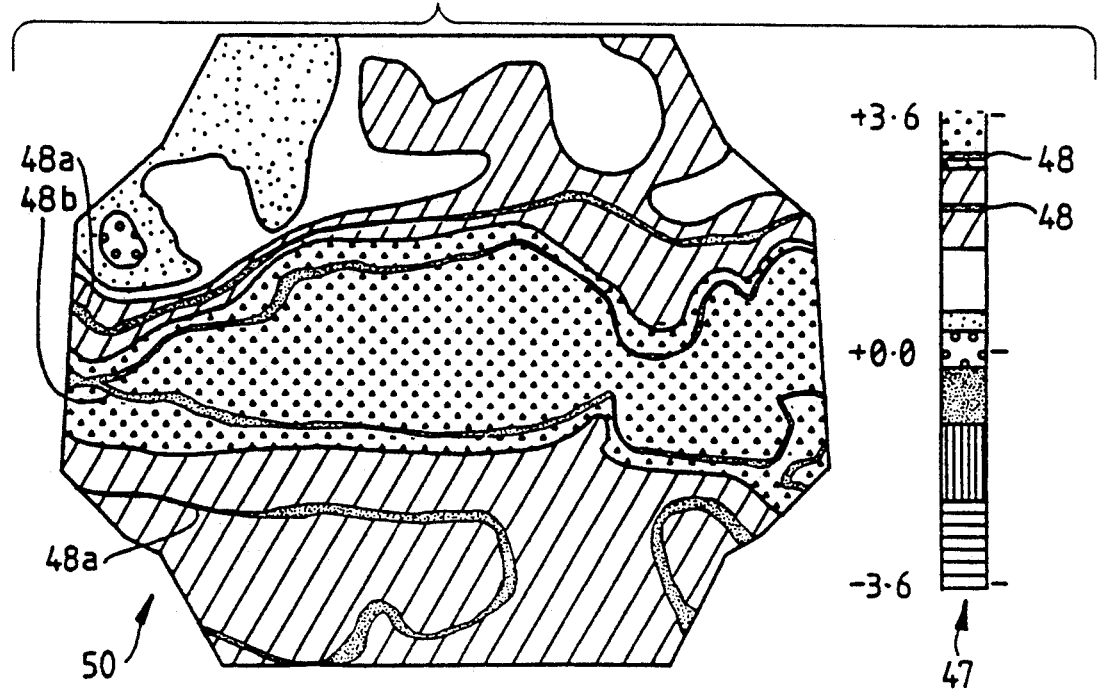
Figure 17A:
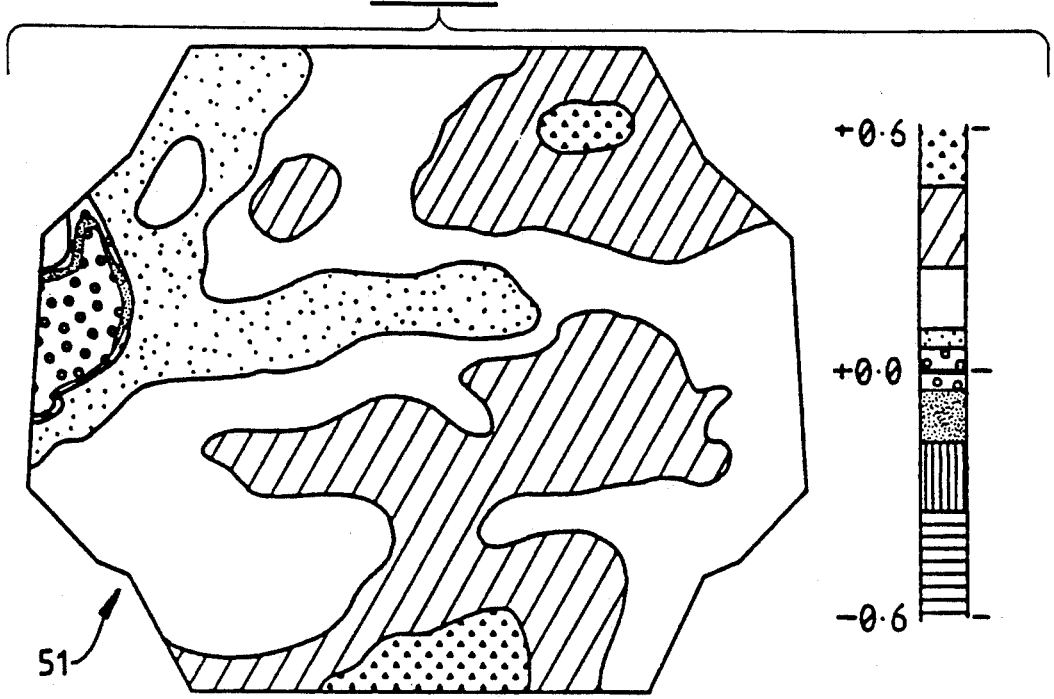
FIGS. 17a and 17b show differences in a topographic distribution of results for a subject under further different viewing conditions, together with the associated distribution of a corresponding Students t-parameter.

The major SSVEP correlate of the increased trial 3 vigilance at presentation is a reduction in SSVEP magnitude. The effects of the instruction to attend to a fault in the circles are illustrated in FIGS. 15A and 15B, 16A and 16B, and 17A and 17B. FIG. 15A illustrates the topographic distribution 44 of the difference between viewings 2 and 3 at the start of the circles or the cueing phase, that is, the differences between FIGS. 19A and 19B. Regions where the trial 3 SSVEP magnitude is less than the trial 2 SSVEP magnitude will thus appear positive. The polarity of the SSVEP changes illustrated in FIG. 15A are then consistent with the Probe-ERP technique, where SSVEP reductions are associated with increased neural activity. The same convention is followed in all other difference maps (FIGS. 16A and 17A). The black area 45 indicates the regions where the differences are zero, on each of these.

Figure 15B:
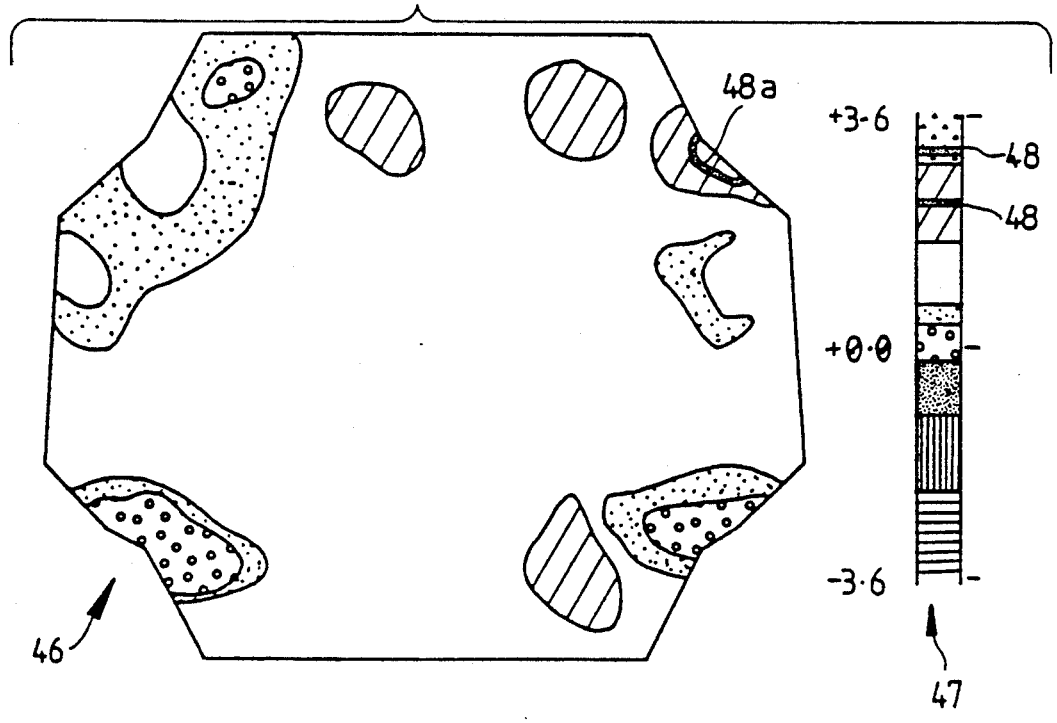

FIG. 15B illustrates the spatial distribution 46 of the Students t- parameter evaluated from a paired t-test. The vertical colour bar 47 relates the colour to the t parameter. The two black horizontal lines 48 in the colour bar in FIG. 15B are set at values of t=1.76 and t=2.97. These correspond to p=0.05 and p=0.005 in a one tailed t-test with 14 degrees of freedom. (Note the orientation of these and subsequent maps is the same as that in FIG. 3.)

All regions showed a reduction, with the occipital and right frontal sites evidencing the largest reduction. While all regions showed an SSVEP reduction in viewing 3, the statistical strength of this effect, as evaluated by the Students t-parameter was low. The Students t-parameter exceeded 1.76 (the value for which p=0.05 in a one tailed t-test with 14 degrees of freedom) only at the right frontal region, as indicated by a black line 48a.

The anticipation phase, ten seconds into the circles, was associated with a large attenuation in the central and occipital regions. FIG. 16A illustrates a topographic map 49 of the differences between viewings 2 and 3 at a time 10 seconds into the circles while FIG. 16B gives the distribution 50 of the Students-t parameter. The differences illustrated in FIG. 16A are apparent at the occipital and centro/parietal sites while the Students t-parameter is larger at the centro/parietal sites. This reflects the smaller intersubject variability in the centro/parieto attenuation.

Figure 17B:
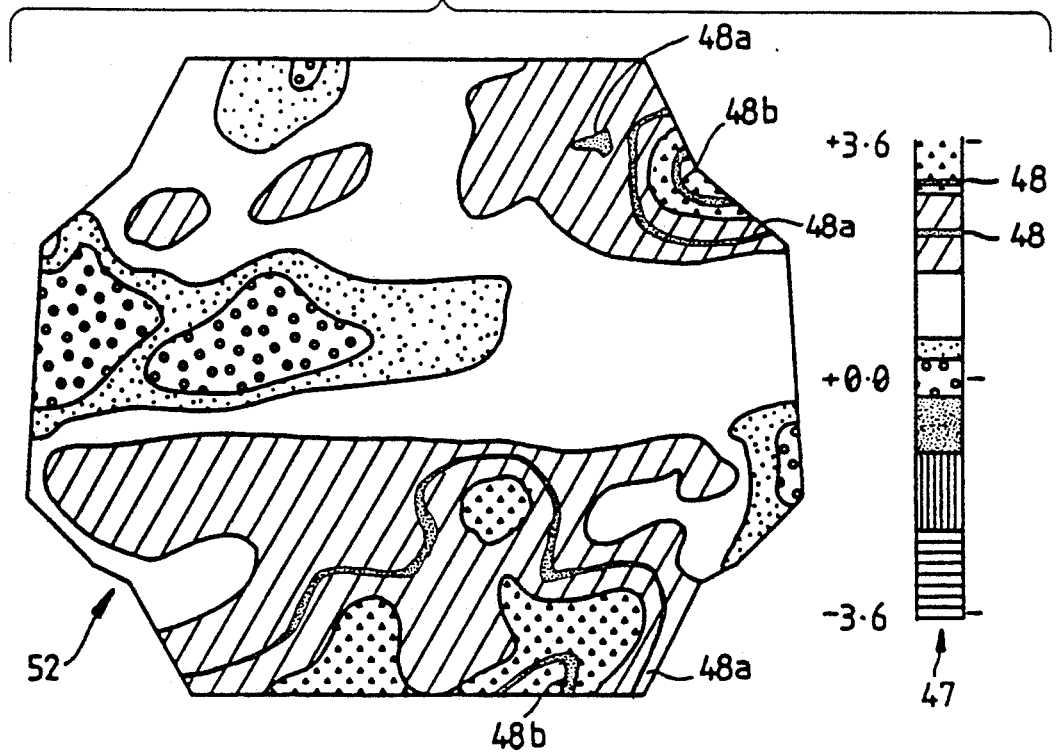

FIG. 17A illustrates a topographic map 51 of the distribution of the differences between viewings 2 and 3 at the time that the target circle appeared while FIG. 17B illustrates the distribution 52 of the corresponding Students t-parameter. The largest effects are restricted to the occipital and right pre-frontal areas.

DISCUSSION OF EXPERIMENT AND RESULTS

In comparing trial 3 with trial 2, the major effect was a reduction in SSVEP magnitude. These reductions, while apparent at each of the three phases, presentation, anticipation and target detection, were only statistically significant at the last two of the phases. The topography of the reductions also differed for each of the phases.

Before considering the significance of these effects, it is appropriate to assess the possible contribution of non-cognitive factors to these changes. Two factors which could contribute to the effects noted are, changes in retinal illuminance resulting from variations in pupil size, and changes in eye fixation position. These were both considered but thought unlikely to account for the effects reported above. In the case of changes in pupil size, increased visual attenuation is known to be associated with pupil dilation. This would increase the effectiveness of the SSVEP stimulus but the results show a reduction in SSVEP magnitude. In the case of changes in fixation position, the mechanism is considered unlikely to contribute to the results as the preliminary experiment indicated that even relatively large deviations in gaze position had no statistically significant effects on the SSVEP. In addition, a very diffuse uniform stimulus was used in the above experiment. Other reports concerning the effects of retinal position on the topography of the VER (Visual Evoked Response) have made reference to relatively small patterned stimuli presented at foveal and juxtafoveal loci. These topographic effects are not seen with unpatterned flash stimuli (Halliday et al 1977). The diffuse stimulus used in the above experiment is incapable of generating the strong differences in retinal illuminance known to be required to demonstrate these type of effects. It is therefore considered unlikely that the reported effects could be significantly influenced by either pupil size or direction of fixation.

While other factors, such as eye movements could have had an effect on the results presented, pupil size and direction of fixation were considered the most likely contaminants.

In comparing trial 3 with trial 2, the dominant effect was a significant attenuation in SSVEP magnitude at most recording sites; this was especially noticeable at occipital/parietal, parieto/central and right frontal sites. Invoking the Probe-ERP technique to interpret these reductions suggests higher regional brain activity during trial 3, compared with trial 2, at sites showing significant attenuation.

The occipital SSVEP attenuation was pronounced during anticipation and target detection. This inferred increase in occipital activity is consistent with reports indicating enhanced occipital/parietal regional cerebral bloodflow and metabolism being correlated with heightened visual attention (Roland 1984; Mazzioti and Phelps 1984).

In comparing trial 3 with trial 2, the right prefrontal region evidenced an SSVEP attenuation during presentation and target detection, although this was only significant during target detection. This indication of increased right prefrontal activity is consistent with neuropsychological evidence for prefrontal involvement in the mediation of attention processes. Prefrontal lesions are associated with an inability to sustain focused attention and an increase in distractibility (Milner & Petrides 1984). Neuropsychological observations demonstrating the role of the prefrontal cortex in attention tasks have also been confirmed by regional cerebral blood flow and neurophysiological studies (Fuster 1980; Fuster et al 1982; Roland 1984). The restriction of the prefrontal attenuation to the right side is also consistent with findings pointing to a specialized role for the right hemisphere in directed attention (Mesulam 1981, Weintraub & Mesulam 1987). This is supported by the observation that right prefrontal lesions are associated with pronounced maze learning deficits in humans (Milner & Petrides 1984) and that increases in right prefrontal regional cerebral bloodflow are seen in directed attention or vigilance tasks (Deutsch et el 1987). The right prefrontal SSVEP attenuation is therefore consistent with the expectation of right prefrontal involvement in the experimental protocol used.

One of the most striking features was the pronounced centro/parietal and occipital SSVEP attenuation during the anticipation phase. While this feature peaked approximately 10 seconds after the appearance of the circles, it was apparent for approximately 50 seconds between presentation and target detection. The temporal and spatial characteristics of this feature are not however further discussed herein. The topography of the centro/parietal attenuation bears some similarity to that of the P3b component of the transient ERP. While the P3b and SSVEP attenuation are quite different phenomena, the similarity of their topographies warrants further comment as it may point to mechanisms common to both. P3b is a diffuse centro/parietal positivity observed approximately 250-450 msec after the presentation of events which are relevant to the subject (Simpson et al 1976; Courchesne et al 1987; Stapleton et al 1987). The inferred behavioral state of the subjects in trial 3 is that of heightened attention. This state is known to be associated with prominent P3b responses (Sutton & Ruchkin 1984). Thus further studies might be designed to explore the relationship between the SSVEP and P3b.

It is suggested that SSPT and transient ERPs offer complementary approaches to the investigation of brain activity. Transient ERPs offer millisecond resolution in the study of rapid brain processes; by contrast the temporal resolution of SSPT is at best measured in seconds. The superior temporal resolution of the transient ERP is, however, obtained at a price. The evaluation of the transient ERP is usually performed by averaging a number of responses. Typically, hundreds to thousands of responses need to be averaged in order to achieve a satisfactory signal to noise ratio for the smaller components Of the ERP. The time required to elicit this number of responses places a limitation on the investigation of any variations in the evoked potentials which may be associated with cognitive processes. If a minimum of one to five minutes is required to elicit the required number of ERPs for subsequent averaging, it is not feasible to investigate processes possessing a time course smaller than this collection time. This is a consequence of the assumption underlying averaging, namely that the evoked potential characteristics are invariant during the period of data collection. Averaged ERPs therefore offer the opportunity of studying rapid processes whose characteristics are invariant over the period of data collection. By contrast, SSPT offers a continuous measure of time varying brain processes which is available over a period extending from seconds to hours. This ability to continuously measure electrophysiological correlates of cognitive processes over an extended period may also have clinical applications in the investigation of attention disorders.

In conclusion the application of SSPT has for the first time, demonstrated changes in SSVEP topography associated with different phases of a visual vigilance task.

APPLICATIONS

1. Clinical Medicine

The primary use for the neuro-psychiatric workstation (NpWS) is in the diagnosis and management of patients with neurological and psychiatric diseases. These include neurological conditions such as stroke, head injury, brain tumor, multiple sclerosis and dementing illnesses such as Alzheimer's disease, multi-infarct dementia, Huntington's disease and Parkinson's disease and psychiatric illnesses such as schizophrenia, bipolar affective disorder, depression end anorexia nervosa.

1.1 Patient Diagnosis: a patient's patterns of brain responses to different cognitive probes are compared with a data bank of responses from normal subjects and from patients with different known neurological diseases. The types of cognitive probes used and the order in which they are tested can be specified by the Examiner, but are usually determined for each patient by the NpWS, using diagnostic algorithms determined by individual patient data provided at the commencement of testing and by ongoing stepwise analysis of the results of current testing. The initial identification of the diagnostic category of each patient's responses is refined by the subsequent application of subgroups of more specific cognitive probes, determined by algorithm from that patient's initial results.

1.2 Patient Management: repeated testing during the course of an illness allows progression or resolution of the illness to be monitored. Each patient's response to treatment can also be measured.

2. Medical Research

The NpWS is a tool for detailed research into the abnormalities of brain function that occur in neurological and psychiatric diseases. Information can be gained about the alterations of brain function that occur early in the course of such diseases and the subsequent effects of progression of the illness. Theories as to the nature and causes of these diseases can be tested. The efficacy of all treatment modalities can be tested, in particular the assessment of new pharmacological agents.

3. Psychology

The NpWS can monitor a variety of brain functions related to mood and emotion, such as attenuation and vigilance, anxiety, awareness and arousal as well as assessing brain function in the course of activities such as reading and learning. It is thus of use in educational, industrial and interventional/therapeutic psychology.

4. Psychology Research

The NpWS allows detailed study of how the brain normally processes the information that it receives. This makes it an ideal research tool for laboratory testing of wide variety of theoretical models of brain functions such as cognition, learning and memory.

CONCLUSION

The above experiment indicates a use or uses to which embodiments of the present invention might be put. However, the versatility of the arrangement makes it clear that a very wide variety of applications are available. Different stimuli might be applied, and different signal processing paths might be provided.

Variations in embodiments of the invention might in particular include the use of gold electrodes rather than those described above, or of a different number or array of electrodes. The flicker stimulus applied might be red light, or might be light of another color, or white light. The flicker stimulus might not be provided entirely separately from the stimulus on the video screen 24, by means of goggles 4, but might comprise for instance an amplitude or brightness variation superimposed on that screen 24. Instead of using a visual flicker stimulus, an entirely different type of stimulus might be applied, such as an auditory instead of a visual stimulus.

The use of a stimulus frequency of 13 Hz is described above but this may be varied, or the stimulus might comprise more than one distinguishable frequency. The flicker stimulus might not be provided entirely separately from the stimulus on the video screen 24, by means of goggles 4, but might comprise for instance an amplitude or brightness variation superimposed on that screen 24. Instead of using a visual flicker stimulus, an entirely different type of stimulus might be applied, such as an auditory instead of a visual stimulus.

The use of a stimulus frequency of 13 Hz is described above but this may be varied, or the stimulus might comprise more than one distinguishable frequency.

It should be noted that FIGS. 15A to 17B are representations of the FIGS. 5 to 7 of Australian patent application number PJ 8006/89, and, in the case of any discrepancy therebetween, the FIGS. 5 to 7 should be taken to be correct, being incorporated herein by reference.

It should further be noted that similar reference numerals should be taken to indicate like features between the various Figures, and in particular between FIGS. 15 to 17 inclusive.

Although full details of circuitry are not given throughout the above description, this is because known circuitry is available for carrying out the various operations, in accordance with the description given, and will be clear to a person skilled in the relevant technology.

I claim:

1. Apparatus for assessing electrical activity of a brain of a subject comprising:
   first stimulus means for generating and applying a repetitive stimulus to the brain;
   second stimulus means for generating and applying to the brain a time varying stimulus relating to a cognitive task; and
   detection means for distinguishing and detecting a steady state response of the brain to said first stimulus, and for detecting a change or changes in said response during a data acquisition period when the repetitive stimulus and a time varying cognitive task stimulus are simultaneously applied to the brain of the subject, wherein the detection means can detect time variations in brain activity of the subject which occur during the data acquisition period.

2. Apparatus according to claim 1, further comprising:
   assessment means for assessing the electrical activity of the brain in terms of said change or changes.

3. Apparatus according to claim 1 wherein said first stimulus means comprises a light source and control means for varying the intensity of the light source in a repetitive manner.

4. Apparatus according to claim 3 wherein said light source comprises an array of light emitting diodes.

5. Apparatus according to claim 3 wherein said detection means comprises at least one electrode for application to the head of said subject to detect electrical activity of the brain, and said stimulus means further comprises optical waveguide means for directing light from said light source to an eye or field of view of the subject, said light source being remote from said electrode, in use.

6. Apparatus according to claim 1 wherein said detection means comprises an array of electrodes for application to the head of said subject to detect electrical activity of the subject's brain, signal processing and data acquisition equipment for processing the outputs of the electrodes, said signal processing and data acquisition equipment comprising a pre-processing portion which, in use, samples said outputs at a rate which is an integral multiple of the frequency of the repetitive stimulus, and an analog to digital converter, the output of said converter being suitable for supply to a computational or storage portion.

7. Apparatus according to claim 6 wherein said signal processing and data acquisition equipment further comprises a computational portion for performing preliminary analysis of said steady state response.

8. Apparatus according to claim 7, further comprising assessment means for assessing the electrical activity of the brain in terms of the change or changes in the response, wherein said assessment means comprises computational means and display control means, said assessment means, in use, carrying out analysis of the steady state response in terms of a spatial distribution with respect to said brain and said display control means, in use, controlling display apparatus to show said spatial distribution.

9. Apparatus according to claim 8 wherein said analysis by the assessment means comprises the assessment of changes in said steady state response and said spatial distribution comprises the distribution with respect to said brain of said changes in the steady state response.

10. Apparatus according to claim 6 wherein said first stimulus means and said pre-processing portion are synchronized.

11. Apparatus according to claim 10 wherein said first stimulus means comprises a frequency generator which controls the sampling rate of said pre-processing portion.

12. Apparatus according to claim 1 wherein said first stimulus means comprises a ramp generator to control the amplitude of the stimulus at start-up such that it increases from zero to a predetermined amplitude at a predetermined rate.

13. Apparatus according to claim 1 further comprising epileptic activity detecting means, comprising means for detecting a significantly large response to said first stimulus, and automatic termination means for terminating said first stimulus on detection of said significantly large response.

14. A method of assessing brain activity of a subject comprising the steps of obtaining a steady state evoked potential of a subject, causing the subject to perform a time varying cognitive task and assessing time variations in the brain activity of the subject on the basis of changes in said potential which occur while said time varying task is being performed by the subject.

15. A method as claimed in claim 14, wherein said potential is obtained by applying a periodically repetitive stimulus to the brain.

16. A method as claimed in claim 15, wherein said periodically repetitive stimulus comprises a signal which sinusoidally varies in intensity.

17. A method as claimed in claim 16, wherein said signal is visual and said potential is a steady state visually evoked potential (SSVEP).

18. A method as claimed in claim 17, including the step of displaying the changes in said SSVEP on a visual display.

19. A method as claimed in claim 18, wherein data acquisition for said assessing step is carried out at a rate which enables high resolution in the time domain of said changes in SSVEP.

20. A method as claimed in claim 18 or 19, including the step of applying an array of electrodes to the head of said subject, obtaining a spatial distribution of said SSVEPs and displaying the changes in respective SSVEPs according to the spatial distribution.

21. A method as claimed in claim 17, wherein the magnitude $M_n$ and phase of the SSVEP is determined by the formula:

$$M_n = \sqrt{(\bar{a}_n)^2 + (\bar{b}_n)^2}$$

$$\theta_n = \text{Tan}^{-1}\left(\frac{\bar{a}_n}{\bar{b}_n}\right)$$

where $a_n$ and $b_n$ are the moving average of the single cycle Fourier coefficients of the repetitive stimulus, $M_n$ is the magnitude of the sinusoidal SSVEP, and $\theta_n$ is the phase difference between the sinusoidal stimulus and the sinusoidal SSVEP.

22. Apparatus for assessing brain activity of a subject comprising first means for obtaining a steady state evoked potential of a subject, second means for causing the subject to perform a time varying cognitive task and third means for assessing time variations in the brain activity of the subject on the basis of changes in said potential which occur while said time varying task is being performed by the subject.

23. Apparatus as claimed in claim 22, wherein said first means includes stimulus means for applying a periodically repetitive stimulus to the brain.

24. Apparatus as claimed in claim 23, wherein said stimulus means generates a signal which sinusoidally varies in intensity.

25. Apparatus as claimed in claim 24, wherein said signal is visual and said potential is a steady state visually evoked potential (SSVEP).

26. Apparatus as claimed in claim 25, further including display means for displaying the changes in said SSVEP.

27. Apparatus as claimed in claim 26, wherein said first, second and third means and display means operate at a rate which enables said display means to display changes in said SSVEP with high resolution in the time domain.

28. Apparatus as claimed in claim 26 or 27, wherein said first means includes an array of electrodes for application to the head of said subject and wherein said third means includes computational means and display control means wherein the third means determines changes in SSVEP in terms of spatial distribution and the display control means controls the display means to show spatial distribution.

29. A method of assessing activity of a brain of a subject comprising the steps of:
applying a periodic control signal having a preselected frequency to the brain of the subject;
obtaining an electroencephalographic (EEG) signal from the subject while said control signal is being applied; and
analyzing the EEG signal to determine the magnitude or phase of that component of the EEG signal which corresponds in frequency to said control signal;
wherein said method further comprises the steps of applying said control signal and a cognitive task stimulus simultaneously to the subject during a data acquisition period;
obtaining and analyzing the EEG signal to determine the magnitude or phase of said component during said data acquisition period;
determining the change in the magnitude or phase of said component of the EEG signal during said data acquisition period; and
assessing time variations in brain activity of the subject in accordance with said change.

30. A method as claimed in claim 29, wherein the control signal comprises a sinusoidal signal.

31. A method as claimed in claim 30, wherein the control signal is a visual signal which is varied in intensity.

32. A method as claimed in claim 31, wherein a semi-reflective screen is placed between the subject and a source of said visual signal and the visual control signal is reflected toward the eye or eyes of the subject.

33. A method as claimed in claim 32, wherein information relating to said cognitive task is displayed to the subject on a television screen.

34. Apparatus for assessing the activity of a brain of a subject comprising:
means for applying a periodic control signal having a predetermined frequency to the brain of the subject;
applying means for applying a cognitive task stimulus to the brain of the subject;
means for deriving the EEG signal from the subject during a data acquisition period in which the control signal and the cognitive task stimulus are simultaneously applied to the brain of the subject; and
analyzing means for determining the change in magnitude or phase of that component of the EEG signal which is attributable to the periodic control signal from one state in which the brain of the subject has applied thereto only the control signal and another state when the brain of the subject has applied thereto both the control signal and the cognitive task stimulus, whereby the analyzing means can assess time variations of brain activity which occur during the data acquisition period.

35. Apparatus as claimed in claim 34, wherein the means for applying the control signal comprises a source or red radiation and means for sinusoidally varying the intensity of the radiation at the predetermined frequency.

36. Apparatus as claimed in claim 35, wherein said frequency is in the range 1 to 100 Hz.

37. Apparatus as claimed in claim 36, wherein said frequency is approximately 10 Hz.

38. Apparatus as claimed in claim 34, wherein said means for applying the control signal comprises as array of LEDs.

39. Apparatus as claimed in claim 38, wherein the LED arrays are mounted upon spectacle frames.

40. Apparatus as claimed in claim 39, wherein said applying means for applying a cognitive task stimulus comprises a television screen and wherein the spectacle frames include semi-reflective screens which permit the subject to view the television screen directly, the screens reflecting radiation from the LED arrays towards the eye or eyes of the subject.

41. Apparatus as claimed in claim 35, wherein the analyzing means includes discriminating means having a sample and hold circuit which holds the output value of said EEG signal at the end of each period of the frequency component of the stimulus.

42. Apparatus as claimed in claim 41, wherein the discriminating means includes an arithmetic unit for calculating the magnitude $M_n$ of the EEG signal at said frequency by taking the square root of the sum of the squares of said output values.

43. Apparatus as claimed in claim 34, wherein said periodic control signal is a visual stimulus and wherein said means for applying a periodic control signal includes support means for supporting at least one semi-reflective screen adjacent to at least one of the eyes of the subject whereby the subject can view directly the visual stimulus, and a source of visible radiation carried by the support means for reflecting radiation from said source towards the eye or eyes of the subject so as to provide said control signal.

44. Apparatus as claimed in claim 34, wherein the analyzing means comprises means for calculating a normalized mean response from the responses of each of a plurality of subjects to the control signal alone, and for determining during the data acquisition period said change in magnitude for each subject by subtracting the normalized mean response from the magnitude of said component of the EEG signal determined for each subject for simultaneously display of the control signal and the cognitive task stimulus.

45. A method of assessing brain activity of a subject comprising the steps of obtaining a steady state evoked potential of a subject, causing the subject to perform a cognitive task and assessing time variations in the brain activity of the subject on the basis of changes in said potential which occur while said task is being performed by the subject.

* * * * *

UNITED STATES PATENT AND TRADEMARK OFFICE
CERTIFICATE OF CORRECTION

PATENT NO. : 5,331,969
DATED : July 26, 1994
INVENTOR(S) : Silberstein

It is certified that error appears in the above-indentified patent and that said Letters Patent is hereby corrected as shown below:

Col. 1, line 35 - delete "Stare" and substitute -- State --.

Col. 3, line 56 - delete "(ads.) and substitute -- (eds.) --.

Col. 4, line 58 - delete "Mallett" and substitute -- Hallett --.

Col. 7, line 19 - delete "Drain" and substitute -- Brain --.

Col. 11, line 28 - delete "lead" and substitute -- load --.

Col. 13, line 26 - delete "normalisatton" and substitute -- normalisation --

Col. 17, line 21 - delete "Schist" and substitute -- Schier --.

Col. 27, line 32 - delete "$a_n$ and $b_n$" and substitute -- $\tilde{a}_n$ and $\tilde{b}_n$ --.

Signed and Sealed this

Fourth Day of October, 1994

Attest:

BRUCE LEHMAN

*Attesting Officer*   *Commissioner of Patents and Trademarks*